United States Patent
Hakimi et al.

(10) Patent No.: US 11,168,295 B2
(45) Date of Patent: Nov. 9, 2021

(54) TISSUE PRINTER

(71) Applicants: THE GOVERNING COUNCIL OF THE UNIVERSITY OF TORONTO, Toronto (CA); SUNNYBROOK RESEARCH INSTITUTE, Toronto (CA)

(72) Inventors: Navid Hakimi, Toronto (CA); Richard Yihsiu Cheng, Toronto (CA); Mohammad Hadi Sotoudehfar, Scarborough (CA); Qing Ba, Toronto (CA); Saeid Amini-Nik, Toronto (CA); Marc G. Jeschke, Toronto (CA); Axel Guenther, Toronto (CA)

(73) Assignees: THE GOVERNING COUNCIL OF THE UNIVERSITY OF TORONTO, Toronto (CA); SUNNYBROOK RESEARCH INSTITUTE, Toronto (CA)

( * ) Notice: Subject to any disclaimer, the term of this patent is extended or adjusted under 35 U.S.C. 154(b) by 368 days.

(21) Appl. No.: 16/340,327

(22) PCT Filed: Oct. 10, 2017

(86) PCT No.: PCT/CA2017/051204
§ 371 (c)(1),
(2) Date: Apr. 8, 2019

(87) PCT Pub. No.: WO2018/064778
PCT Pub. Date: Apr. 12, 2018

(65) Prior Publication Data
US 2020/0040291 A1 Feb. 6, 2020

Related U.S. Application Data

(60) Provisional application No. 62/405,704, filed on Oct. 7, 2016.

(51) Int. Cl.
*B33Y 30/00* (2015.01)
*C12M 1/26* (2006.01)
(Continued)

(52) U.S. Cl.
CPC .............. *C12M 33/00* (2013.01); *A61L 27/38* (2013.01); *A61L 27/60* (2013.01); *B29C 64/209* (2017.08);
(Continued)

(58) Field of Classification Search
CPC ......... B33Y 30/00; B33Y 50/02; B33Y 80/00; A61L 27/38; A61L 27/60; C12M 21/08
See application file for complete search history.

(56) References Cited

U.S. PATENT DOCUMENTS 9,266,286 B1 * 2/2016 Starodubtsev ........ B29C 64/106
2009/0208577 A1 8/2009 Xu et al.
(Continued)

FOREIGN PATENT DOCUMENTS

CA 2856063 A1 5/2013
CN 105751510 A 7/2016
(Continued)

OTHER PUBLICATIONS

International Search report for PCT/CA2017/051204 dated Feb. 15, 2018.
(Continued)

*Primary Examiner* — Yung-Sheng M Tsui
(74) *Attorney, Agent, or Firm* — Hill & Schumacher

(57) ABSTRACT

Disclosed herein is a bioprinter that enables the in situ formation of architected planar biomaterials and tissues by translating a printer head along a deposition surface, such as skin wounds. In handheld configurations of of the instrument, cell-laden biopolymer solutions are perfused through a moving microfabricated printhead and deposited onto a (Continued)

stationary planar surface or a wound. The printer head may be translated via a drive mechanism. Different embodiments of the instrument are disclosed form vivo application in small animals, as well as for large animal and clinical application. A stationary embodiment of the instrument is well suited for the continuous formation and roll-to-roll processing of planar biomaterials and tissues.

20 Claims, 24 Drawing Sheets

(51) Int. Cl.
B33Y 50/02 (2015.01)
B29C 64/209 (2017.01)
B29C 64/393 (2017.01)
B29C 64/236 (2017.01)
A61L 27/38 (2006.01)
A61L 27/60 (2006.01)
C12M 3/00 (2006.01)
B33Y 80/00 (2015.01)
B29L 31/00 (2006.01)

(52) U.S. Cl.
CPC .......... *B29C 64/236* (2017.08); *B29C 64/393* (2017.08); *B33Y 30/00* (2014.12); *B33Y 50/02* (2014.12); *C12M 21/08* (2013.01); *B29K 2995/0056* (2013.01); *B29L 2031/7532* (2013.01); *B33Y 80/00* (2014.12)

(56) References Cited

U.S. PATENT DOCUMENTS

| 2014/0012225 | A1 | 1/2014 | Yoo et al. | |
| 2015/0140058 | A1 | 5/2015 | Tumey et al. | |
| 2015/0142159 | A1* | 5/2015 | Chang | B29C 64/106 700/119 |
| 2016/0038655 | A1* | 2/2016 | Weisman | B29C 64/106 264/0.5 |
| 2016/0303789 | A1* | 10/2016 | Bogue | B33Y 30/00 |
| 2017/0190118 | A1* | 7/2017 | Mire | B29C 64/393 |
| 2017/0217088 | A1* | 8/2017 | Boyd, IV | B29C 64/209 |
| 2019/0134902 | A1 | 5/2019 | Jiang et al. | |
| 2020/0030491 | A1* | 1/2020 | Weisman | B33Y 30/00 |

FOREIGN PATENT DOCUMENTS

| CN | 106073788 A | 11/2016 |
| CN | 106867902 A | 6/2017 |
| WO | 2016019078 A1 | 2/2016 |
| WO | 2017181773 A1 | 10/2017 |
| WO | 2017205663 A1 | 11/2017 |
| WO | 2018014440 A1 | 1/2018 |

OTHER PUBLICATIONS

Kang, H. W. et al. A 3D bioprinting system to produce human-scale tissue constructs with structural integrity. Nature Biotechnology 34, 312-+, doi:10.1038/nbt.3413, (2016).

Xu, T., Jin, J., Gregory, C., Hickman, J. J. & Boland, T. Inkjet printing of viable mammalian cells. Biomaterials 26, 93-99, (2005).

Norotte, C., Marga, F. S., Niklason, L. E. & Forgacs, G. Scaffold-free vascular tissue engineering using bioprinting. Biomaterials 30, 5910-5917, (2009).

Melchels, F. P., Dhert, W. J., Hutmacher, D. W. & Malda, J. Development and characterisation of a new bioink for additive tissue manufacturing, Journal of Materials Chemistry B 2, 2282-2289, (2014).

Ferris, C. J., Gilmore, K. J., Beirne, S., McCallum, D. & Wallace, G. G. Bio-ink for on-demand printing of living cells. Biomaterials Science 1, 224-230, (2013).

Onoe, H. et al. Metre-long cell-laden microfibres exhibit tissue morphologies and functions. Nature Materials 12, 584-590, (2013).

Griffin, D. R., Weaver, W. M., Scumpia, P. O., Di Carlo, D. & Segura, T., Accelerated wound healing by injectable microporous gel scaffolds assembled from annealed building blocks. Nature Materials 14, 737-744, (2015).

Navarro, F. et al. Sprayed keratinocyte suspensions accelerate epidermal coverage in a porcine microwound model. Journal of Burn Care & Research 21, 513, (2000).

Falanga, V. et al. Autologous bone marrow derived cultured mesenchymal stem cells delivered in a fibrin spray accelerate healing in murine and human cutaneous wounds. Tissue Engineering 13, 1299-1312, (2007).

Au, A. K., Fluynh, W., Horowitz, L. F. & Folch, A. 3D printed microfluidics, Angewandte Chemie International Edition, (2016).

Leng, L., McAllister, A., Zhang, B., Radisic, M. & Günther, A. Mosaic hydrogels: one step formation of multiscale soft materials. Advanced, Materials 24, 3650-3658, (2012).

\* cited by examiner

TISSUE PRINTER

FIELD

The present disclosure relates to a printer device for conformally printing layers of biopolymers or engineered tissues onto surfaces for in vitro and/or in vivo applications or wounded areas.

BACKGROUND

Skin is the largest organ of the body and possesses a unique layered organization of cells and extracellular matrix components. This spatial composition is in part responsible for organ function. Patients who suffer from skin injuries such as patients with acute complex wounds and severe burns often lose large skin regions, rendering them vulnerable to opportunistic infections and dehydration. In regard to full thickness wounds where the dermis, epidermis, and hypodermis are destroyed, current treatment options include covering the wound site to provide a temporary barrier against bacterial and water loss, then isolating skin from healthy regions of the body to redistribute across the wounded region as a meshed graft, referred to as autografting. Since their introduction by Earl C. Padgett in 1937, dermatomes have been used to surgically harvest skin from donor sites for autografting, but they create another wound. Meshing allows the coverable wound area to exceed the size of the harvest site. Less frequently practiced micrografting allows covering an area up to hundred-fold greater than the harvest site[1]. While autografting is the gold standard in current clinical practice, in patients with large wounds, complex wounds or large burns there is not enough donor skin available for autografting, leaving a large area ungrafted or uncovered which is associated with poor outcomes. Skin substitutes or even cell therapies have been introduced to overcome this limitation.

A large number of skin substitutes have been developed based on both natural and synthetic polymers. While tissue-engineered skin substitutes are commercially available, the long required times for cell expansion/growth and their high cost prevent their broad clinical adaptation. One of the current gold standards is a collagen-based wound dressing that was developed more than 35 years ago[2], allows residual healthy cells to migrate through the provided pores, and requires 2-3 weeks for a new dermal layer to be reconstituted. Direct deposition of cells onto the wound area have been proposed as a faster and more effective treatment, but the lack of extracellular matrix components results in a lack of structural integrity and skin tissue architecture. Cell spray technologies have been clinically applied to homogeneously deposit autologous cells at low concentrations, without expansion onto partial thickness wounds and have demonstrated improved outcomes[3].

Increasingly, additive manufacturing approaches have been employed to create cell-laden, architected biopolymeric constructs that recapitulate aspects of the structure of intact human tissues[4-6]. Demonstrated 3D bioprinting approaches include filament and microdrop extrusion[7-8], stereolithography[9,10], inkjet-printing[11,12], laser-assisted printing[13,14] and replica molding[15]. They are primarily used for in vitro studies with different cell types and biopolymers. The latter are sometimes referred to as "bioinks" and include both natural (e.g., alginate, collagen, fibrin, gelatin, agarose, dextran) and synthetic (e.g., poly ethylene glycol and polycaprolactone) biopolymers. Protein-based materials of choice include collagen, the most abundant protein in mammalian tissues, and fibrin, a protein involved in various steps of wound healing. Cells favor these soft gels with high porosity and water content[16,17]. However, any manipulation of centimeter-sized bioprinted sheets made from such mechanically weak gels is a challenging task without substrate support. One strategy to overcome this limitation is utilizing a multimaterial approach that involves printing a support structure from a synthetic polymer[7]. Another challenge is the long gelation times on the order of several minutes typically associated with protein-based biopolymers.

Strategies to mitigate this limitation have been the addition of a more rapidly gelling biopolymer[18], and to print and subsequently remove a sacrificial material. While current 3D bioprinting approaches have been successful in defining engineered constructs with tissue-relevant architecture in vitro, translation to in vivo is a multi-step, demanding process that relies on the use of synthetic supporting materials as scaffolds exceeding the mechanical properties of natural tissues. On the other hand, current approaches for the in-situ formation of tissues demonstrated via using injectable hydrogels[19], self-assembly of microscale building blocks at the wound bed[20], spraying of rapidly crosslinking cell-containing hydrogel precursors[21,22], and various photo cross-linkable cartilage fillers and adhesives[23-25] lack deterministic control over the spatial organization of cells and biopolymers.

SUMMARY

Disclosed herein is an instrument that enables the in situ formation of architected planar biomaterials and tissues by translating a printer head along a deposition surface. In handheld embodiments of the instrument, cell-laden biopolymer solutions are perfused through a moving microfabricated printer head and deposited onto a stationary planar surface or a wound. The printer head may be translated via a drive mechanism. Different embodiments of the instrument are disclosed for in vivo application in small animals, as well as for large animal and clinical application. A stationary embodiment of the instrument is well suited for the continuous formation and roll-to-roll processing of planar biomaterials and tissues.

The present disclosure provides bioprinter for controlled in-situ formation and deposition of biopolymeric sheets and planar tissues on surfaces, comprising:

a) support frame and a printhead attached to the support frame, the printhead including a first array of extrusion channels and at least a second array of extrusion channels located with respect to the first array such that in operation the first array is proximally adjacent to the surface, an end section of the printhead having a width W such that the first and second arrays span the width W;

b) a first reservoir attached to the frame, the first array of extrusion channels being in flow communication with the first reservoir of biopolymer to be extruded onto the surface, a second reservoir of liquid attached to the frame, the second array being in flow communication with the second reservoir of liquid to be extruded along with the extruded biopolymer, and including a first dispensing mechanism associated with the first reservoir being configured to dispense biopolymer at a flow rate of QM, and a second dispensing mechanism associated with the second reservoir being configured to dispense the liquid at a flow rate of QC;

c) a drive mechanism attached to the frame such that when activated by the operator, the printhead is driven along the surface located a vertical height H above the surface at a preselected velocity V;

d) a controller connected to the drive mechanism and the first dispensing mechanism and programmed such upon activating the drive mechanism, the first dispensing mechanism dispenses biopolymer at the flow rate QM a layer of thickness t, which satisfies the condition $QM=W \cdot V \cdot H(6(t/H)-6(t/H)^2+3(t/H)^2 \, (\mu C/\mu M)/(6(t/H) \, (\mu C/\mu M)-6(t/H)+6)$.

The drive mechanism may be configured to provide variable velocities V, and wherein the controller is programmed with instructions to control the first dispensing mechanism to responsively adjust the flow rate QM such that for a given velocity V the flow rate conditions are maintained.

The second dispensing mechanism may be operably coupled with the controller and is configured to dispense the liquid at the flow rate QC which satisfies the condition $$QC=0.5W \cdot V \cdot (H-t)$$

The drive mechanism may be configured to provide variable velocities V, and wherein the controller is programmed with instructions to control the first and second dispensing mechanisms to responsively adjust the flow rates QM and QC such that for a given velocity V the conditions are maintained.

The exit section of the printhead may include an overhanging section extending outwardly from a top surface of the second array, the overhanging protruding section extending outwardly from the exit section by a length L.

The length L may be equal to or greater than the value of H.

The first array of extrusion channels may be in flow communication with the first reservoir via a bifurcating channel network comprised of a first channel connected to the first reservoir which bifurcates into two channels which further bifurcates until a final number of channels equals a number of extrusion channels in the first array, and an end of each channel is adjacent an end of a corresponding extrusion channel in the first array, and wherein the second array of extrusion channels are in flow communication with the second reservoir via a bifurcating channel network comprised of a first channel connected to the second reservoir which bifurcates into two channels which further bifurcates until a final number of channels equals a number of extrusion channels in the second array, and an end of each channel is adjacent an end of a corresponding extrusion channel in the second array.

Hydraulic diameters of the channels in the bifurcating channel networks decrease from each inlet to each exit going from the reservoir to the printer head in accordance with Murray's law.

The bioprinter may further comprise a handle for allowing a user to grasp and use the bioprinter during dispensing operations so that the bioprinter is a handheld bioprinter.

The drive mechanism may comprise a pair of axel mounted rollers connected to the drive mechanism, and wherein the printer head is positioned between the rollers, and wherein the end section includes a circular guidance feature maintains a consistent gap height between the channel device exit and deposition surface regardless of changing the deposition angle, and wherein during operation upon activation of the drive mechanism, the pair of axel mounted rollers are rotationally driven such that the handheld bioprinter moves along the surface at the velocity V.

The drive mechanism may comprise a roller connected to the drive mechanism, and wherein the roller is positioned behind the printhead, and wherein end section contains a circular guidance feature to maintain a consistent gap height between the channel device exit and deposition surface regardless of changing the deposition angle, and wherein during operation upon activation of the drive mechanism, the roller is rotationally driven such that the handheld bioprinter moves along the surface at the velocity V.

The drive mechanism may comprise a translation mechanism attached to the frame, the printhead being mounted on the translation mechanism, the translation mechanism being configured to move the printer head at the velocity V with respect to the surface.

BRIEF DESCRIPTION OF DRAWINGS

Embodiments will now be described, by way of example only, with reference to the drawings, in which.

DETAILED DESCRIPTION

Figure 1:
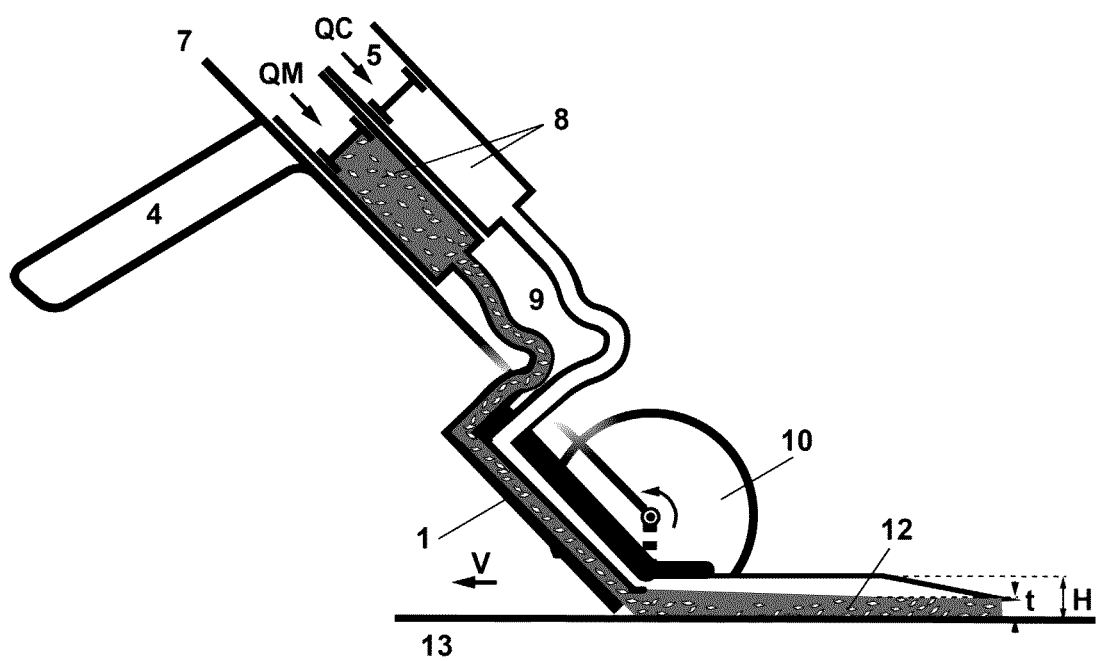
FIG. 1. Schematic illustration of handheld bioprinter in embodiment with side-mounted wheels.

Various embodiments and aspects of the disclosure will be described with reference to details discussed below. The following description and drawings are illustrative of the disclosure and are not to be construed as limiting the disclosure. The figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary", "illustrative" and "for example" mean "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

3D bioprinting strategies aim at reconstituting structural elements of native tissues by controlling the position of different cell types and extracellular matrix components. The provided microenvironment and spatial organization influence cell migration, elongation, clustering, proliferation, differentiation, and function. Current bioprinting platforms offer promising in-vitro results but are not yet compatible with clinically relevant settings. Higher print rates, reduced preparation and wait times, and compact solutions for on-site deposition or transfer of organ-scale printed tissues are required to ultimately treat patients with acute and complex wounds that are amongst the most impactful clinical and economical challenges. Disclosed herein is a handheld skin printer that overcomes these limitations by in-situ formation of wound-adhesive skin substitutes.

The present disclosure provides bioprinter for controlled in-situ formation and deposition of biopolymeric sheets and planar tissues on surfaces, comprising:

a) support frame and a printhead attached to the support frame, the printhead including a first array of extrusion channels and at least a second array of extrusion channels located with respect to the first array such that in operation the first array is proximally adjacent to the surface, an end section of the printhead having a width W such that the first and second arrays span the width W;

b) a first reservoir attached to the frame, the first array of extrusion channels being in flow communication with the first reservoir of biopolymer to be extruded onto the surface, a second reservoir of liquid attached to the frame, the second array being in flow communication with the second reservoir of liquid to be extruded along with the extruded biopolymer, and including a first dispensing mechanism associated with the first reservoir being configured to dispense biopolymer at a flow rate of QM, and a second dispensing mechanism associated with the second reservoir being configured to dispense the liquid at a flow rate of QC;

c) a drive mechanism attached to the frame such that when activated by the operator, the printhead is driven along the surface located a vertical height H above the surface at a preselected velocity V;

d) a controller connected to the drive mechanism and the first dispensing mechanism and programmed such upon activating the drive mechanism, the first dispensing mechanism dispenses biopolymer at the flow rate QM a layer of thickness t, which satisfies the condition $QM = W \cdot V \cdot H(6(t/H) - 6(t/H)^2 + 3(t/H)^2 (\mu C/\mu M)/(6(t/H) (\mu C/\mu M) - 6(t/H) + 6)$.

In an embodiment the drive mechanism is configured to provide variable velocities V, and wherein the controller is programmed with instructions to control the first dispensing mechanism to responsively adjust the flow rate QM such that for a given velocity V the flow rate conditions are maintained.

In an embodiment the second dispensing mechanism may be operably coupled with the controller and is configured to dispense the liquid at the flow rate QC which satisfies the condition $$QC = 0.5 W \cdot V \cdot (H-t)$$

In an embodiment the drive mechanism is configured to provide variable velocities V, and wherein the controller is programmed with instructions to control the first and second dispensing mechanisms to responsively adjust the flow rates QM and QC such that for a given velocity V the flow rate conditions are maintained.

In an embodiment the exit section of the printhead includes an overhanging section extending outwardly from a top surface of the second array, the overhanging protruding section extending outwardly from the exit section by a length L.

In an embodiment the length L is equal to or greater than the value of H.

In an embodiment the first array of extrusion channels are in flow communication with the first reservoir via a bifurcating channel network comprised of a first channel connected to the first reservoir which bifurcates into two channels which further bifurcates until a final number of channels equals a number of extrusion channels in the first array, and an end of each channel is adjacent an end of a corresponding extrusion channel in the first array, and wherein the second array of extrusion channels are in flow communication with the second reservoir via a bifurcating channel network comprised of a first channel connected to the second reservoir which bifurcates into two channels which further bifurcates until a final number of channels equals a number of extrusion channels in the second array, and an end of each channel is adjacent an end of a corresponding extrusion channel in the second array.

In an embodiment the hydraulic diameters of the channels in the bifurcating channel networks decrease from each inlet to each exit going from the reservoir to the printer head in accordance with Murray's law.

In an embodiment the bioprinter further comprises a handle for allowing a user to grasp and use the bioprinter during dispensing operations so that the bioprinter is a handheld bioprinter.

In an embodiment the drive mechanism comprises a pair of axel mounted rollers connected to the drive mechanism, and wherein the printer head is positioned between the rollers, and wherein the end section includes a circular guidance feature maintains a consistent gap height between the channel device exit and deposition surface regardless of changing the deposition angle, and wherein during operation upon activation of the drive mechanism, the pair of axel mounted rollers are rotationally driven such that the handheld bioprinter moves along the surface at the velocity V.

In an embodiment the drive mechanism comprises a roller connected to the drive mechanism, and wherein the roller is positioned behind the printhead, and wherein end section contains a circular guidance feature to maintain a consistent gap height between the channel device exit and deposition surface regardless of changing the deposition angle, and wherein during operation upon activation of the drive mechanism, the roller is rotationally driven such that the handheld bioprinter moves along the surface at the velocity V.

In an embodiment the drive mechanism comprises a translation mechanism attached to the frame, the printhead being mounted on the translation mechanism, the translation mechanism being configured to move the printer head at the velocity V with respect to the surface.

The tissue printing device will now be described with reference to the Figures and the following parts list.

PARTS LIST

| Label | Part | Description |
| --- | --- | --- |
| 1 | Printer head | Printhead manufactured using one of the manufacturing processes: 3D-printing, thermal embossing, or micro-injection molding. Device bottom translates proximal to deposition surface. Device exit of width W, optional protruding section of length L, positioned at height H above deposition surface. Biomaterial or tissue sheet of thickness t produced. |
| 2 | Front block | Serves to mount drive mechanism to base plate. |
| 3 | Temperature control | Controls temperature of solutions within reservoirs and printer head, prior to extrusion. Thermoelectric element, cooler, aluminum syringe jacket, two wells for pressure-controlled delivery of secondary biopolymer solution. |
| 4 | Handle | Used for holding of instrument by human operator. Enables positioning of handheld bioprinter above target surface or wound. May include switch to initiate controlled sheet deposition. |
| 5 | Dispensing system | Modular dispensing system controlling flow rates QM and QC for solutions supplied from separate reservoirs. Dispensing systems individually consist of a stepper motor, a belt-drive with pulleys, a screw-based linear translation mechanism, a push pin and a push button. |
| 6 | Reservoir scaffold | |
| 7 | Base plate | Plate for mounting of reservoirs, dispensing system, handle, and printer head holder |
| 8 | Reservoirs | Biopolymer solution supplied from corresponding reservoir at flow rate QM, and flow confining solution at flow rate QC. Reservoirs may include standard BD syringes with sizes (1 cc, 3 cc, 5 cc, 10 cc, 20 cc). |
| 9 | Tubing | Delivers solutions from reservoirs to printer head. |
| 10 | Roller driving system | Defines deposition speed V along surface. Consists of one or two rollers, a belt drive with two pulleys, one shaft, and one stepper motor. |
| 11 | Printer head holder | Holding mechanism for accommodating printer head and adapter. Spring-loaded to gently push printer head with consistent force against deposition surface. |
| 12 | Printed biomaterial or tissue sheet | Homogenous or heterogeneous biopolymer or tissue sheet |
| 13 | Surface or Wound | Deposition or wound surface. |
| 14 | Switch | Start/stop switch to drive motor activity. |
| 15 | Conveyor belt | Conveyor belt moving at velocity V. |

Disclosed herein is a bioprinter for controlled deposition of biopolymeric sheets onto surfaces which includes a support frame having a printer head attached thereto. The precursor solution that constitutes the printed sheet is a mixture of natural or synthetic biopolymer solution with cells and/or growth factors, but is not limited to extracellular matrix materials or any structural analogs. Synthetic polymers approved for clinical use and shown to be effective may be a potential application due to its advantage of large-scale synthesis without batch-to-batch variation. The biopolymer is loaded onto one of the handheld printers (FIG. 1, 11, 12, 13) reservoir including but not limited to standard BD syringes ranging from 1-20 cc or 3D printed features, and maintained at a desired storage temperature. As the biopolymer solution is perfused through the printer head and deposited on site of the injury, it is polymerized and thus solidifies. The solidification can be induced via different mechanisms that include ionically induced, pH induced, and temperature induced gelation, as well as enzymatic reactions and polymerization induced by ultraviolet light and combinations thereof. For natural biopolymers like fibrinogen, the crosslinking can be initiated from the plasma in the wound bed. The printer head includes a first array of extrusion channels and a second array of extrusion channels located with respect to the first array such that in operation, as the printer is dispensing or extruding one or more layers, the first array is proximally adjacent to the surface on which the layer(s) is being deposited. A biopolymer that may contain a cross-linker for premixing is generally perfused through the first array of channels so that a uniform coating is applied to the wound, or another surface depending on how the bioprinter is configured, discussed hereinafter. A confining or secondary fluid that may contain a cross-linker is perfused through the second array of channels and delivered to the biopolymer coating on the side adjacent to the wound or deposition surface. If a cross-linker was added to the confining fluid, the cross-linker is diffusively transported into the biopolymer layer.

The end section of the printer head (see FIG. 8, 9, 10, 19) from which the layer is being dispensed has a width W such that the first and second arrays span this width W. A first reservoir is attached to the base plate and is in upstream flow communication with the first array of extrusion channels which when in operation will contain the biopolymer of viscosity $\mu M$ to be extruded directly onto the surface. A second reservoir of a confining or secondary liquid is attached to the frame which is in upstream flow communication with the second array through which the secondary liquid of viscosity $\mu C$ is co-extruded on top of the first layer. A dispensing mechanism associated with the first reservoir is configured to supply the biopolymer at a volumetric flow rate of QM, and another dispensing mechanism associated with the second reservoir is configured to supply the secondary or confining liquid at a volumetric flow rate of QC.

Figure 22:
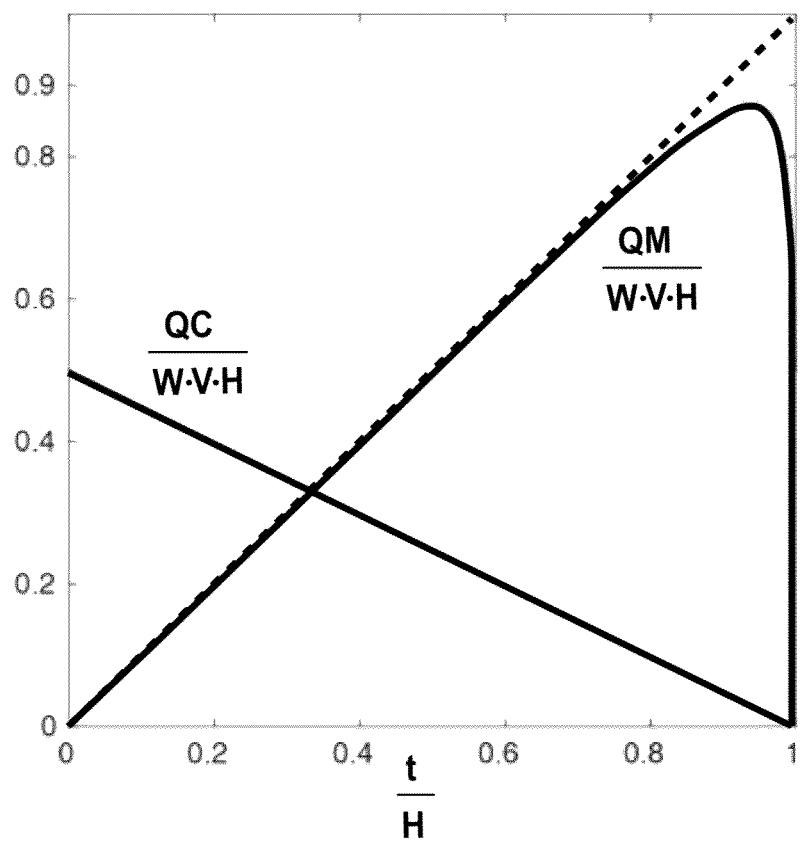
FIG. 22. Analytical model prediction (solid lines) indicating QC/(W·V·H) and QM/(W·V·H) conditions required for viscosity ratio μC/μM=0.01 to fulfill zero pressure gradient condition. Dashed line corresponds to QC/(W·V·H)=t/H. Gelation neglected in model.

The bioprinter includes a drive mechanism attached to the frame such that when activated, the print head is driven along the surface located a vertical height H above the surface at a preselected velocity V. A controller is connected to the drive mechanism and the first dispensing mechanism and the controller is programmed such upon activating the drive mechanism, the first dispensing mechanism dispenses biopolymer of thickness t at the flow rate QM which satisfies the condition:

$$QM = W \cdot V \cdot H(6(t/H) - 6(t/H)^2 + 3(t/H)^2 (\mu C/\mu M))/(6(t/H)(\mu C/\mu M) - 6(t/H) + 6)$$

see FIG. 22.

In most cases the confining solution is of much lower viscosity, $\mu C$, compared with the viscosity of the biopolymer solution, $\mu_M$, and the relationship simplifies to $QM = W \cdot V \cdot t$. W is a design feature of the print head and thus is fixed, and is usually selected to be in a range from about 5 mm to about 30 mm. As discussed later, the forces across the print head are preferably even to ensure uniform dispensing laterally across the width of the first array of extrusion channels in the print head. The thickness t of the dispensed biopolymer is typically in the range in range from about 0.01 mm to about 1 mm, see FIGS. 21 and 23.

The thickness t should be less than approximately 1 mm in order to allow nutrient supply for cells without vascularization. The thickness of the biopolymer sheet may be selected according to the target tissue thickness in healthy skin, and the severity of the wound. If the skin injury is only partial thickness and the dermal layer remains intact, the sheet thickness that is to be printed is about 0.3 mm. For basal lamina, only 0.01 mm sheet of an engineered composition is necessary. If the dermal layer is also damaged, (full thickness injuries) thicker sheets are necessary. Dermal and epidermal layer in the skin have different thicknesses on the body based on the injury. The layers are printed sequentially or co-extruded simultaneously. Each layer can have different composition and cell type load (see FIGS. 25, 26, 28 and 29).

Figure 16:
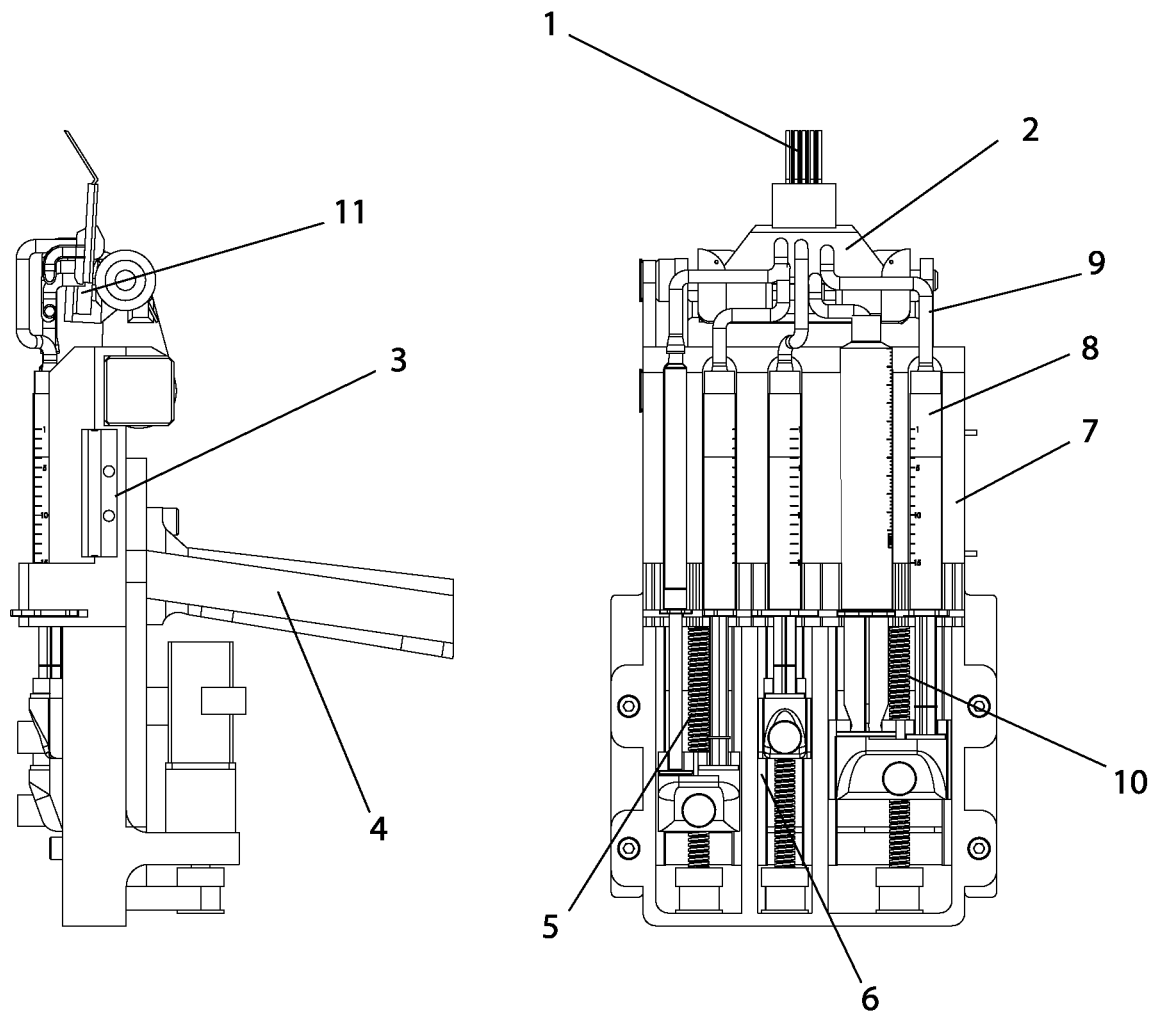
FIG. 16. Side and frontal views of handheld bioprinter in embodiment with rollers mounted behind printer head.

V is typically in the range from about 1 mm/sec to about 20 mm/sec, velocities in the range of 1 to 8 mm/s may be preferred. For the case of slow gelation (e.g., thick sheet, no premixing) a lower velocity may be preferred (see FIGS. 14, 16, 24) where the measurement and model predictions for sheet thickness are provided, modifying the velocity V corresponds to the change in sheet material thickness t. The product of print head width W and velocity V determines the coverable area per time. For large skin injuries (40% burn in an average size male translates to approximately one square meter) there is an interest in covering wounds rapidly. With a W=20 mm printhead the printer can cover one square meter in less than half an hour. H should be at least twice the target sheet thickness, t. H may vary between 0.15 mm and 2 mm. t may vary between 0.01 mm and 1 mm.

Figure 15:
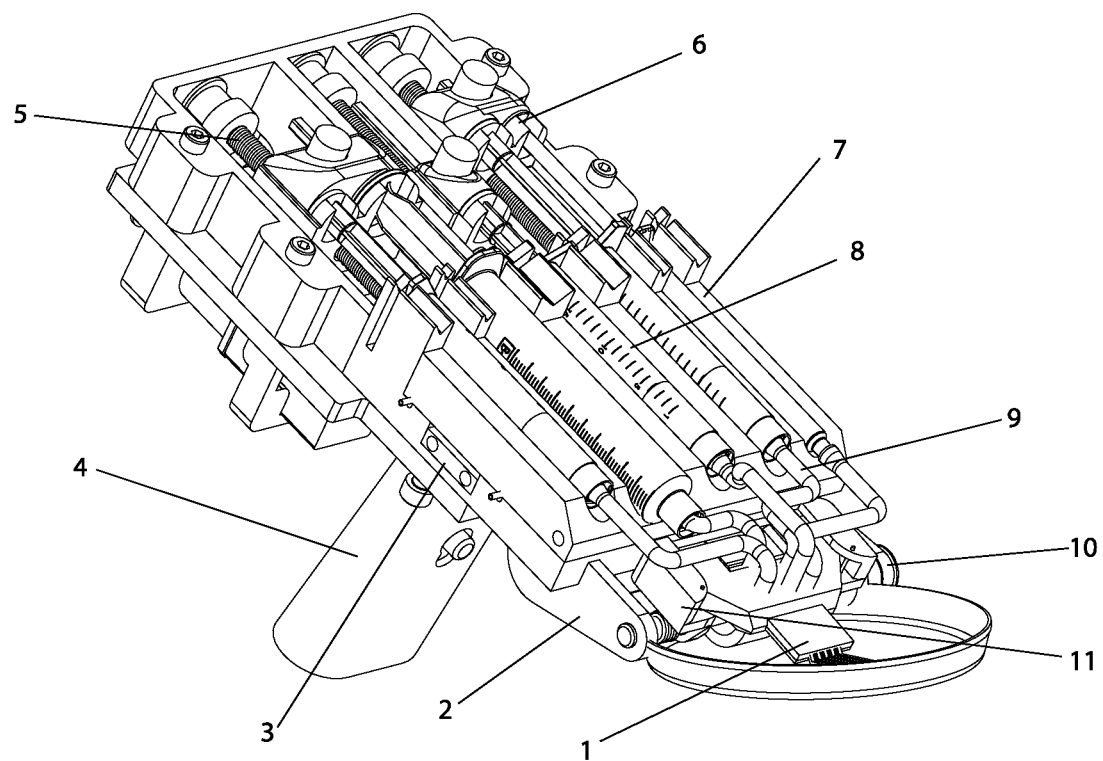
FIG. 15. Perspective view of handheld bioprinter in embodiment with rollers mounted behind printer head.

As noted above, the dispensing mechanism and drive mechanism are configured to give a biopolymer flow rate QM which satisfies the flow condition $QM = W \cdot V \cdot t$. The operator decides the target thickness. Velocity V is selected depending on the gelation kinetics. Flow rate QM (and QC) is for a given print head design (L, H, and W) calculated using the above relationship and selected by the operator on a computer through a user interface. In an embodiment this will be done via a single switch on the handle (see FIG. 2, and Part 4 in FIG. 15).

The bioprinter may be configured to provide variable velocities V, and the controller is programmed with instructions to control the first dispensing mechanism to responsively adjust the flow rate QM such that for a given velocity V the flow rate conditions are maintained.

In an embodiment the flow rate of the liquid, QC, may also be controlled to satisfy certain conditions. In this case the second dispensing mechanism is also connected to the controller and is configured to dispense the liquid at the flow rate QC which satisfies the condition $$QC = 0.5 W \cdot V \cdot (H-t).$$

When the flow rates QM and QC are both selected to satisfy the above conditions, the drive mechanism is configured to provide variable velocities V, and the controller is programmed with instructions to control the first and second dispensing mechanisms to responsively adjust the flow rates QM and QC such that for a given velocity V the above-noted flow rates are maintained.

The controller may be a computer microprocessor with a visual display indicating the flow rates of QM and QC, and the velocity of bioprinter motion in the lateral direction V. Values for QM, QC, and V can be input through the computer and the corresponding motor speeds will be updated in real time. An on/off switch located on the handle will start or stop the extrusion and/or lateral motion of the handheld bioprinter.

Figure 17:
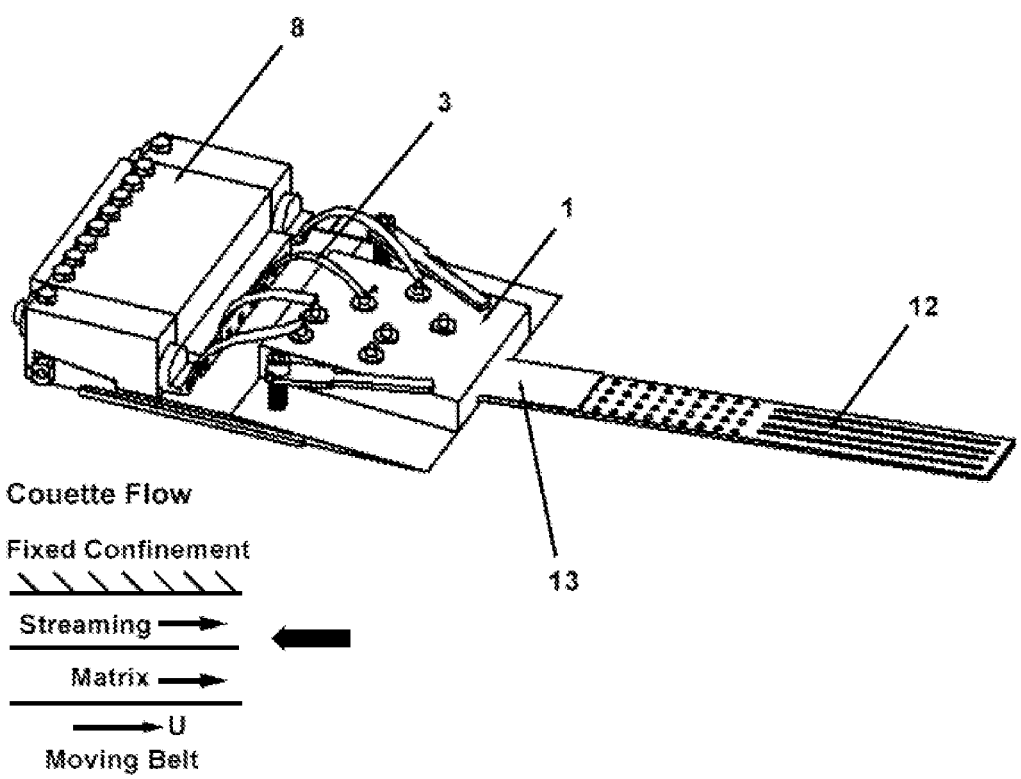
FIG. 17. Schematic illustration of continuous sheet formation in embodiment where printer head is mounted in spatially fixed position above moving conveyor surface. Biopolymer sheet produced from one or multiple biopolymer precursor solutions that may contain colloidal payloads. Cross-linker solution (top) and biopolymer solution (bottom) form stratified flow at printer head exit, initiating gelation at interface.

The bioprinter may be configured such that the exit section of the printer head includes an overhanging section extending outwardly from a top surface of the second array. This overhanging protruding section extends outwardly from the exit section by a length L which is equal to or greater than the value of H as shown in FIG. 17.

The first array of extrusion channels are in flow communication with the first reservoir via a bifurcating channel network comprised of a first channel connected to the first reservoir which bifurcates into two channels which further bifurcates until a final number of channels equals a number of extrusion channels in the first array wherein the downstream end of each channel is adjacent an end of a corresponding extrusion channel in the first array. The second array of extrusion channels are in flow communication with the second reservoir in the same way as the first array described above.

Alternatively, the biopolymer and the cross linker can be pre-mixed within the printer head. In this case, the fluids that are being delivered from the reservoirs pass through a microfabricated mixer prior to the extrusion channels. In this configuration, the flow confining solution may consist of a buffer solution without promoting gelation. The sheet thickness in this case is $t=((QM+QC,PREMIX)/W*V)$, where QC,PREMIX is the volumetric flow rate of the crosslinker added to the biopolymer solution for pre-mixing.

Alternatively, an ultraviolet light source may be positioned directly on top of the cartridge exit. The solidification may be initiated by free radical polymerization of the biopolymer. The biopolymer is mixed with a photo initiator before being loaded on to the handheld bioprinter, or the photo initiator can be mixed inline on the print head. As the biopolymer is being extruded on site of the injury, a sheet of ultraviolent light generated by a light emitting or laser diode may serve to polymerize the biopolymeric sheet. The sheet thickness in this case is $t=(QM/W*V)$.

The solidification mechanism can also be applied by thermal gelation. In this embodiment, the biopolymer solution is either kept in either a heated or cooled condition within the reservoir and print head. As the biopolymer exits the cartridge and comes in contact with the wounded area, it gels and solidifies. The sheet thickness is $t=(QM/W*V)$.

The hydraulic diameters of the channels in the bifurcating channel networks decrease from each inlet to each exit going from the reservoir to the printer head to increase the flow resistance at the distribution channels and ensure the uniformity of the deposited sheet One way of increasing the flow resistance in each step of bifurcation is decreasing the hydraulic diameter of the daughter branches in accordance with Murray's law. Murray's law predicts the dimensions of branches in a transport network to minimize the work attributed to the transport and maintenance of the medium. For n daughter branches splitting from a common mother branch, Murray's law states that $r^3 = r_1^3 + r_2^3 + r_3^3 + \ldots + r_3^n$ where r is the radius of the parent branch and are the radii of the daughter branches (Sherman, T F, *J Gen Physiol*, 1981). Due to the increase in channel width while keeping the channel depth constant for subsequent branching architecture, there is a decrease in resistance to reduce the pressure subsequently the chance of biomaterial clogging (see FIG. 8).

A non-limiting example of the reservoir and dispensing mechanism illustrated in the Figures described hereinafter is a syringe with a plunger with the plunger connected to a motor, such as a stepper motor which drives, via a toothed motor shaft, a toothed gear belt which is engaged with a toothed gear on the plunger so that the controller acts to control the rotation of the stepper motor shaft. It will be appreciated that this embodiment is not limited to stepper motors, servomotors, DC motors, pneumatic drivers, or other types of linear drives.

In addition, other types of dispensing mechanisms may be used other than the above described motor, gear and toothed gear belt. For example, a square wave pressure signal can be applied to the air-filled reservoir headspace. A solenoid valve controlled with an Arduino Mega microcontroller to change the frequency and duty cycle of the pressure signal can be used (see FIG. 7). The spot size and volume can be controlled by adjusting the upper pressure level and the valve open times. Target volumetric flow rates QM and QC may also be indirectly selected by individually controlling the head pressure of reservoirs using a pressure regulator. The relationship between the applied inlet pressure and the obtained flow rate can be obtained for the different fluids from calibration measurements.

Figure 5:
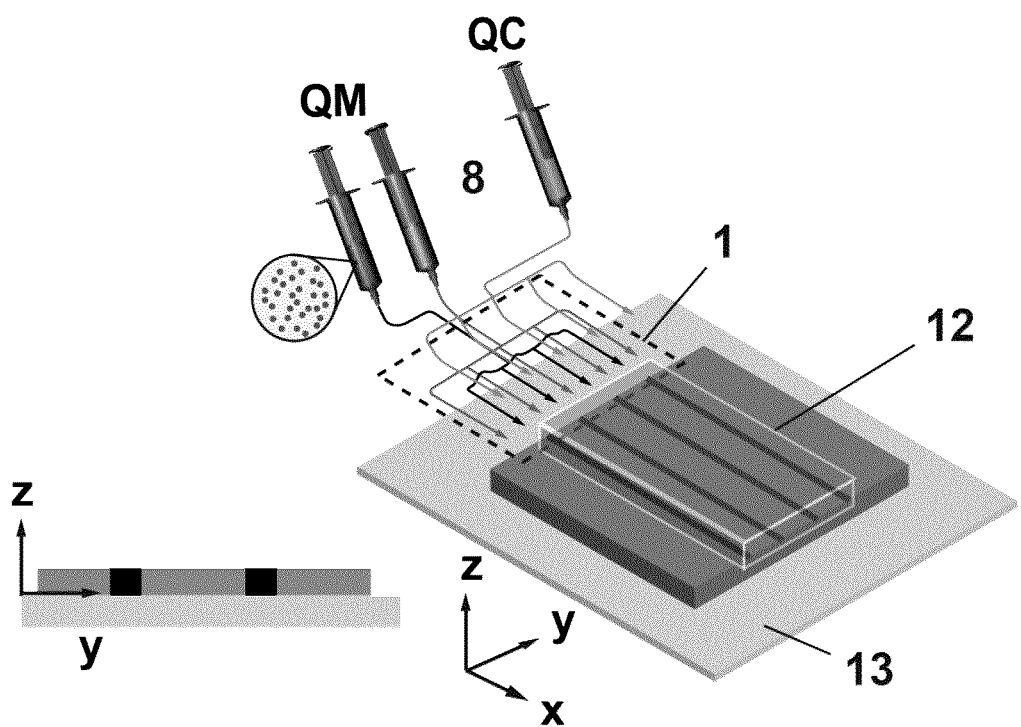
FIG. 5. Schematic illustration for stripe patterned sheet formation.
Figure 32:
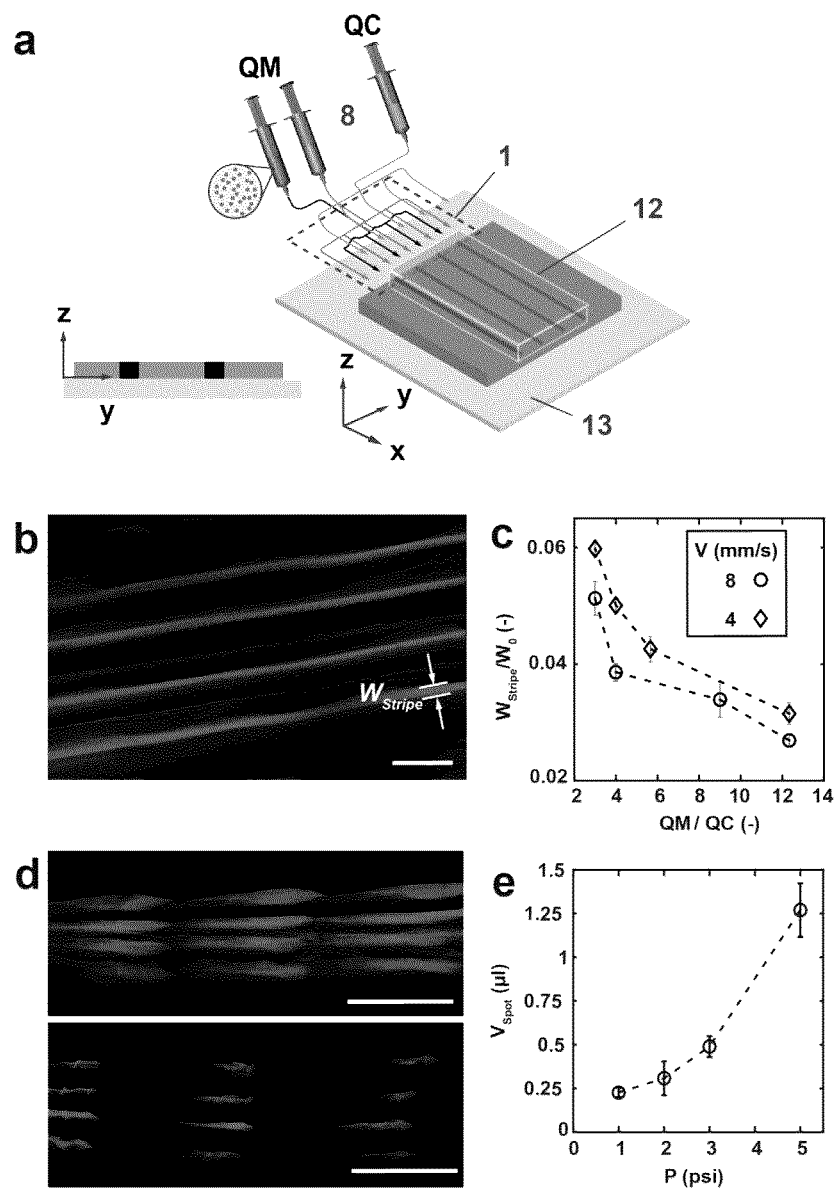
FIG. 32. (a) Schematic of biomaterials and cells organized into stripe patterns using microfabricated printer head. (b) Representative confocal image of striped monolayer. (c) Relative stripe width $w_{stripe}/w_0$ as function of flow rate ratio. (d) Representative images for pressure-controlled spotting. (e) Spot volume as function of reservoir head pressure for 200 ms actuation time. Scale bars 2 mm (b), 6 mm (d). Data obtained for sheets prepared with handheld bioprinter embodiment 1.
Figure 33:
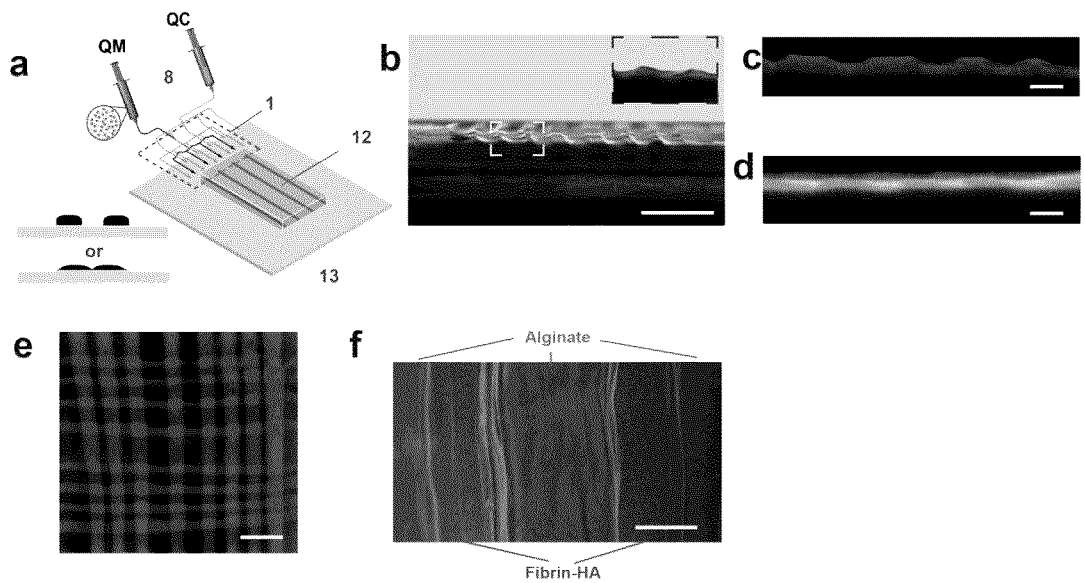
FIG. 33. (a) Schematic of biomaterials and cells organized into undulated sheets or parallel fibers using microfluidic cartridge. (b) Representative bright field image of an adulated sheet with 8 peaks. The image is capture at 4 degrees. The insert shows a zoomed in image of two neighboring peaks at 2 degrees. (c) Representative reconstructed confocal image of cross-section of a sheet with four peeks. (d) Representative reconstructed confocal image of cross-section of a bi-layered sheet. The first layer (green) is homogenous. The top layer is made of four parallel stripes. (e) Mesh pattern printed by printing eight parallel stripes perpendicular to one another. (f) Representative multi-material organization of Fibrin-HA stripes within alginate sheet. Scale bars 5 mm (b), 0.2 mm (c, d), 4 mm (e), 0.5 mm (f). Data obtained for sheets prepared with handheld bioprinter embodiment 1.

The microfluidic printhead can allow the organization of the biomaterial in the planar direction. Multiple reservoirs can be attached to the distributing channel within a layer and deposited in a stripe configuration. The geometry and the widths of the deposited stripes can be controlled by tuning the relative flow rates of the biopolymer solutions coming from each reservoir (see FIGS. 5, 6, 32).

Figure 6:
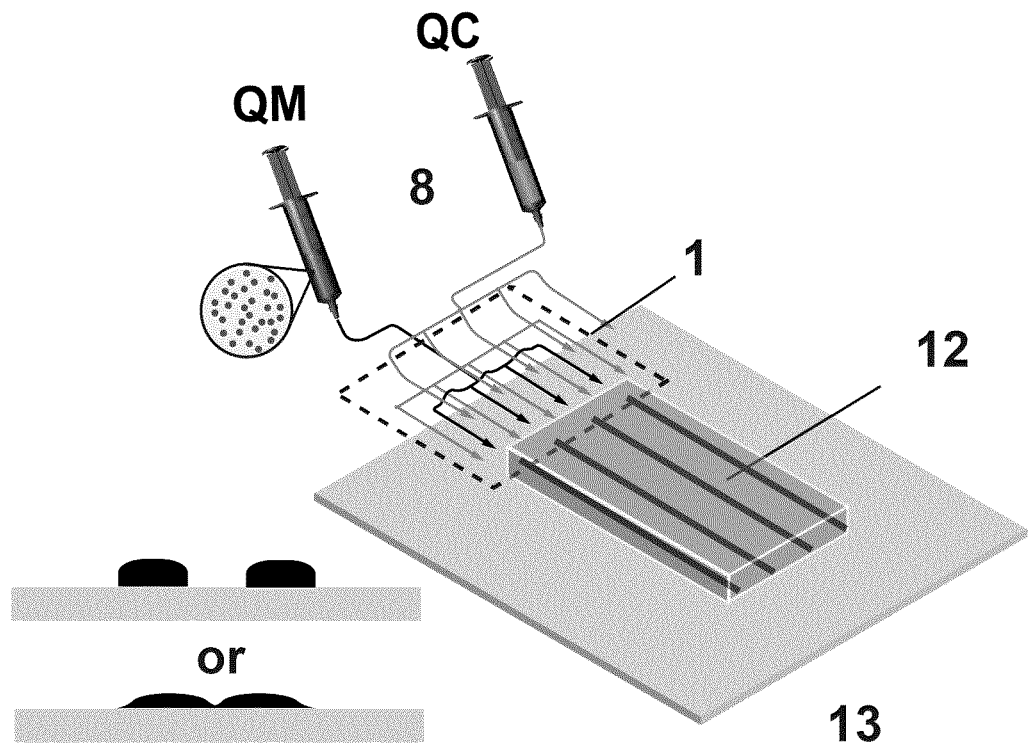
FIG. 6. Schematic illustration for deposition of parallel fibers and undulated sheets.

The crosslinker and biopolymer can be coextruded in a planar geometry to achieve undulating sheets or parallel fibers (see FIG. 6, 33).

Figure 4:
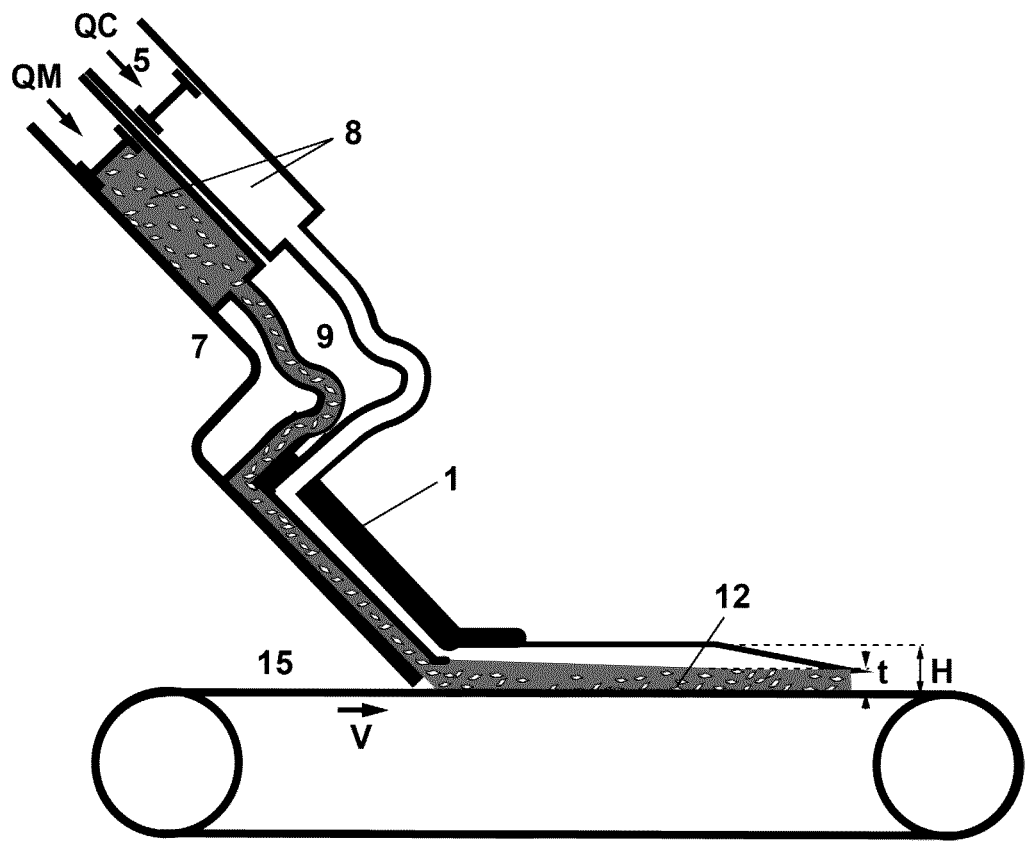
FIG. 4. Schematic of handheld bioprinter in embodiment with spatially fixed printer head depositing onto conveyor belt.
Figure 18:
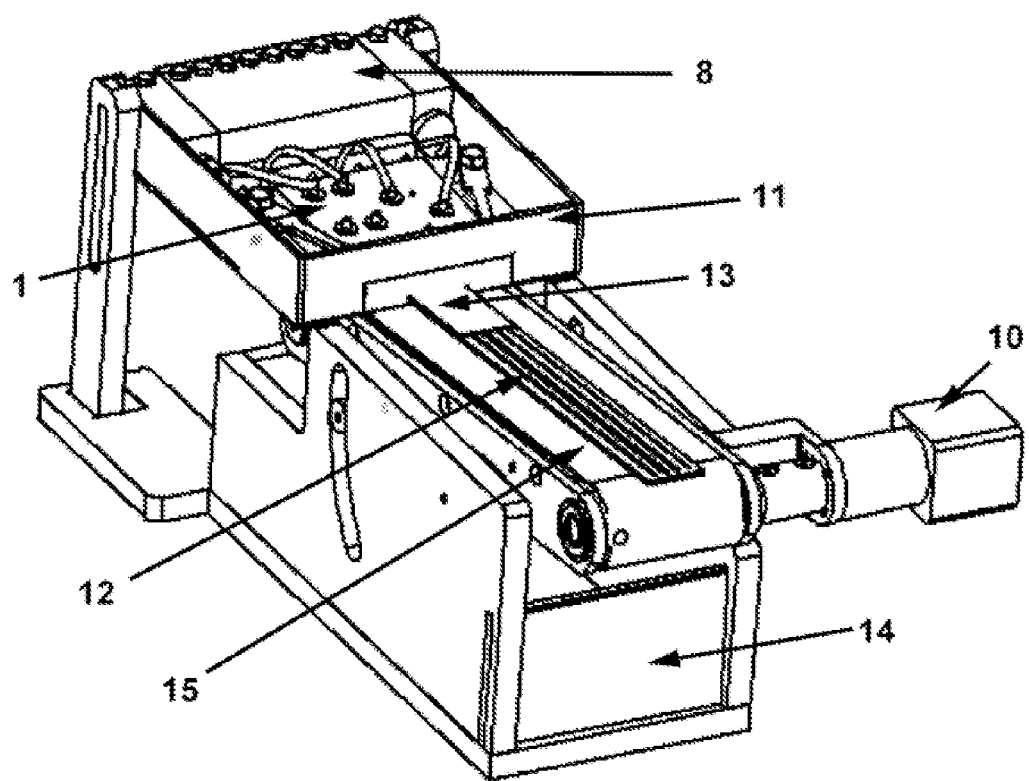
FIG. 18. Schematic illustration of experimental configuration for sheet formation in configuration with conveyor belt. A two-layered print head is supplied with polymer and cross-linker solutions. Solutions are supplied by reservoirs either via pressure-controlled delivery or via flow rate controlled delivery from external syringe pumps. A stationary printer head with protruding section (top) and a moving conveyor belt (bottom) establish hydrodynamic boundary conditions for sheet formation and gelation. A stepper motor translates belt at velocity V.
Figure 19:
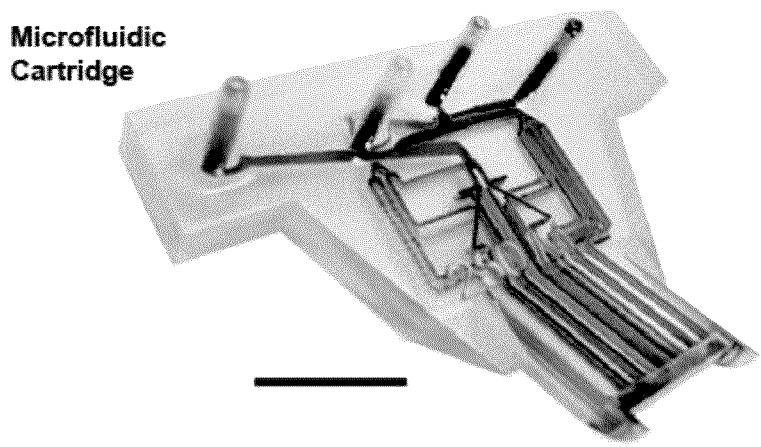
FIG. 19. Photograph of 3D printed microfabricated printer head fabricated for bioprinter embodiment 1. Scale bar 10 mm.

The tissue bioprinter may be configured to be mounted independent of an human operator, for example in cases where it is desired to produce a coating on a moving conveyor (see FIGS. 4, 18), for instance to enable continuous roll-to-roll processing of biomaterial and tissue sheets.

In another embodiment, the bioprinter may be configured to be handheld by a clinician running the device over the surface with one hand. In this situation the bioprinter is configured to have a handle to be gripped by the clinician. The handle may be ergonomically designed with a velocity control switch or button for the clinician to engage as the printer is moved over the wound area of the patient. In one embodiment the velocity control switch is configured to give one set velocity when the switch is engaged, in another embodiment the velocity control switch may be configured to give a variable velocity depending on how far the clinician depresses the switch.

For the handheld bioprinter the drive mechanism may comprise a pair of axel mounted rollers connected to the drive mechanism, and wherein the printer head is positioned between the rollers, and the angle between the end of the printer head and the surface is maintained by the human operator. The exit section of the print head is located one drive wheel radius below the axis of rotation and the direction of extrusion is tangential to the drive wheel. This configuration allows for consistent sheet deposition even during small changes of deposition angle. The bottom side of the print head is positioned in close proximity of the deposition surface and H is maintained by design. In the case where the printer head is positioned above a conveyor at a fixed angle the height H can be selected independently and maintained over the course of the deposition. During operation upon activation of the drive mechanism, the pair of axel mounted rollers are rotationally driven by a motor, such as, but not limited to, a stepper motor, toothed gear and gear belt forming part of the drive mechanism, such that the handheld bioprinter moves along the surface at the selected velocity V.

Figure 2:
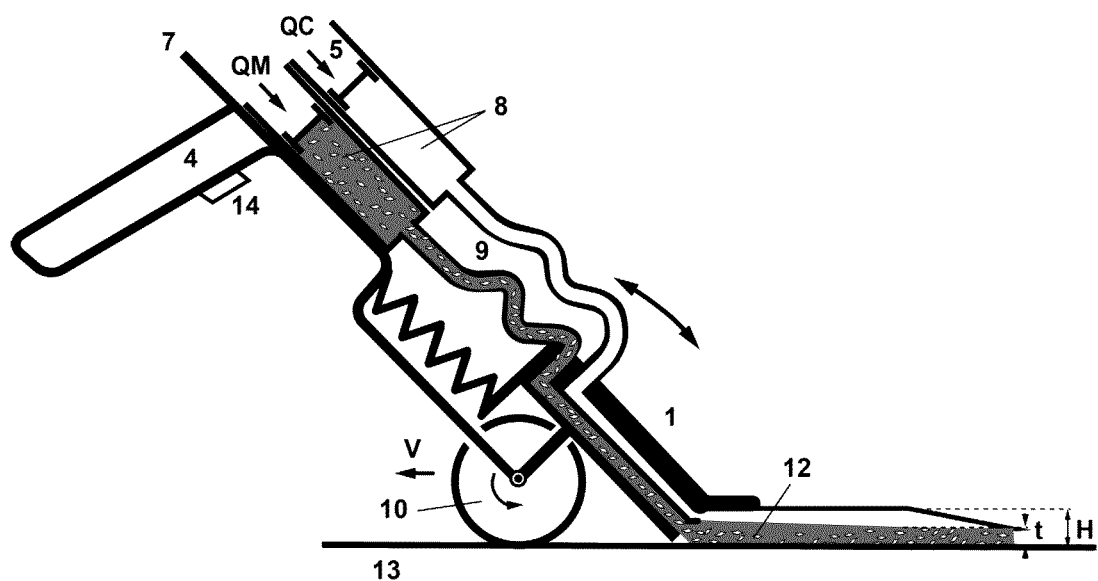
FIG. 2. Schematic illustration of handheld bioprinter in embodiment with drive mechanism behind printer head.
Figure 14:
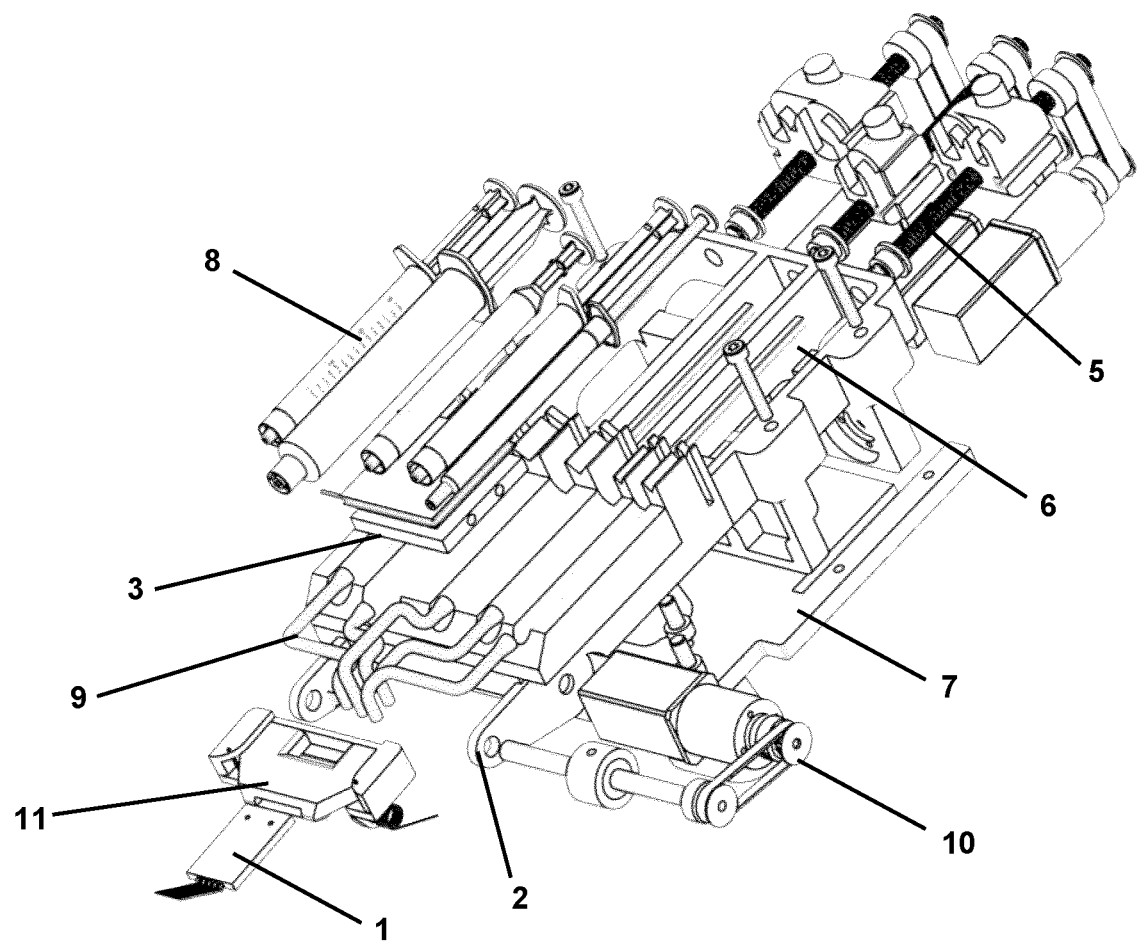
FIG. 14. Exploded view of handheld bioprinter in embodiment with rollers mounted behind printer head.

Alternatively, the drive mechanism comprises a roller connected to the drive mechanism, and the roller is positioned behind the print head (FIG. 2). In this case, the print head is mounted in such a fashion that it may rotate around the rotational axis of the roller. The end section of print head out of which the biopolymer is extruded is brought into contact with the deposition surface by a spring mechanism. During operation upon activation of the drive mechanism, the roller is rotationally driven by a motor such as, but not limited, to a stepper motor, toothed gear and gear belt forming part of the drive mechanism such that the handheld bioprinter moves along the surface at the selected velocity V (FIG. 14, 15). The drive mechanism is not restricted to stepper motors, toothed gears and toothed gear belts. Other types of drive mechanisms may be comprised of servo motors, and pneumatic drives.

Alternatively, the movement can be achieved by the operator actively moving the printer. In this embodiment, the movement is measured with an idler wheel, or a contact free motion detection method, like any motion sensor, an accelerometer, or laser light. In this case, the movement is registered and calculated by the computer and the syringe pumps or air pressure governing the flow rate of the biopolymer and crosslinker is controlled and adjusted in a closed loop.

Figure 3:
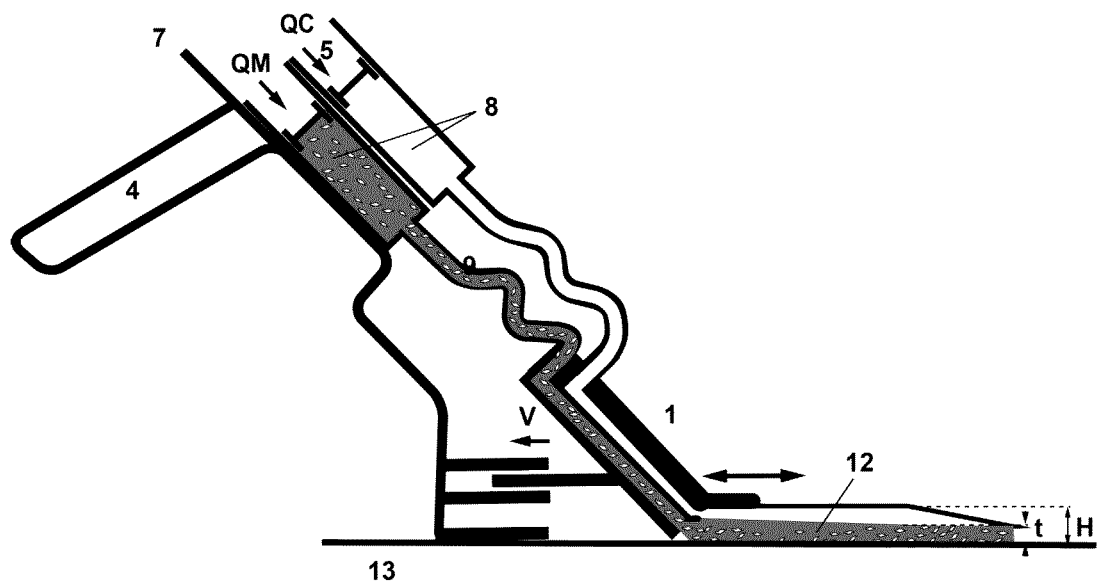
FIG. 3. Schematic of handheld bioprinter in embodiment with scanning printer head.

Alternatively, the handheld bioprinter may be configured to remain stationary during deposition and only the printer head is moved via a translation mechanism forming part of the drive mechanism with the printer head being mounted on the translation mechanism (FIG. 3). The translation mechanism is connected to the controller which is programmed to instruct the translation mechanism to move the printer head at the selected velocity V with respect to both the surface and the rest of the handheld bioprinter.

Figure 20:
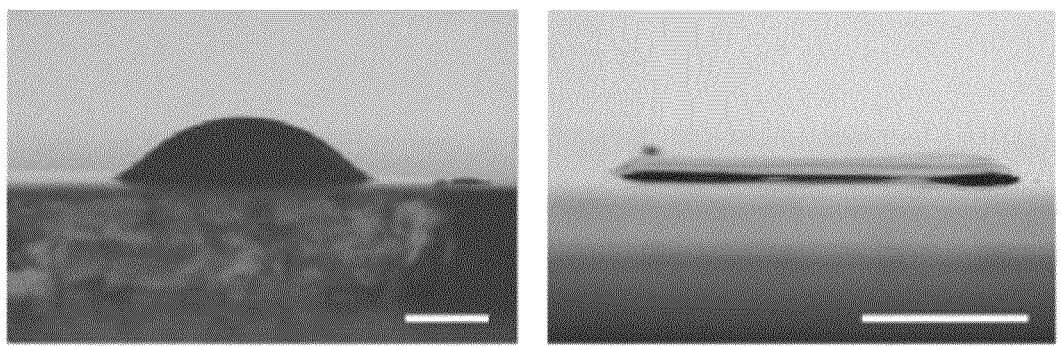
FIG. 20. Comparison of side view images after manual deposition of 100 μl droplet of fibrin/HA biopolymer solution (left) and sheet deposited using handheld bioprinter embodiment 1 (right). Agarose substrates hydrated with cross-linker solution were used in both cases. Images were acquired at 4-degree-angle.

The bioprinter device enables the controlled deposition of biopolymeric sheets onto a substantially flat or curved surfaces. The materials are deposited onto flat or curved surfaces, or directly onto wound areas. Sheets may have a homogeneous or heterotypic composition (FIG. 20, 27, 32, 33, 34). Aspect ratios (width to height, w/t) are between 10 and 3,000.

Figure 30:
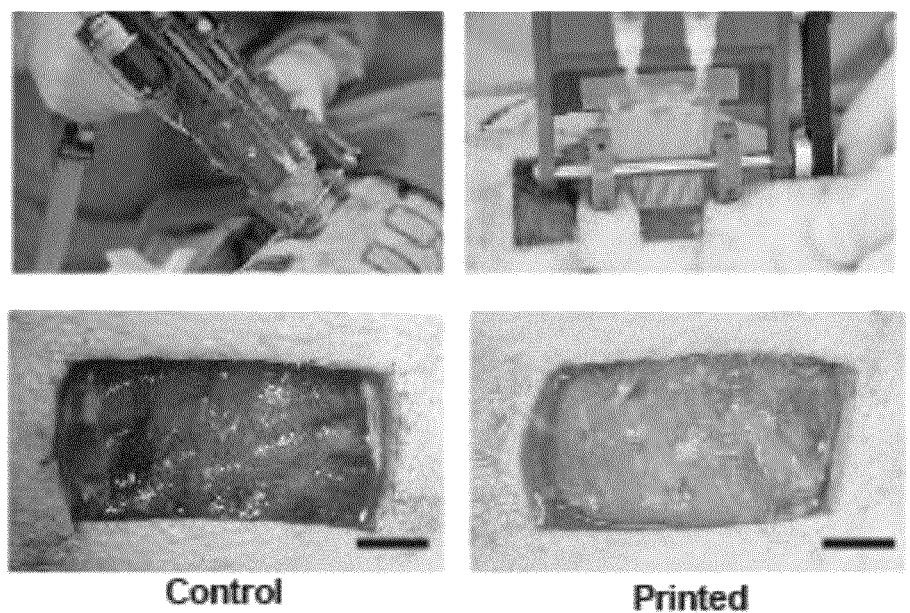
FIG. 30. Top: Representative photograph showing in situ deposition of 0.25 mm thick fibrin-HA/collagen sheet on top of a full thickness excisional porcine wound using handheld Skin Printer and close-up view of deposition within wound area with microfluidic cartridge. Bottom: Day 0 control area and wound 5 min after deposition of a layer of biomaterial. Scale bars are 10 mm. Data obtained for sheets prepared with handheld bioprinter embodiment 1.

The bioprinter device enables the controlled deposition of biopolymeric sheets onto a substantially flat or curved surfaces (FIG. 30, 31, 34). The materials are deposited onto flat or curved surfaces, or directly onto wound areas. Sheets may have a homogeneous or heterotypic composition. Aspect ratios (width to height, w/t) may be in a range between 10 and 3,000.

The print mechanism is not limited to producing homogenous layered sheets. Using the printer disclosed herein, more complex tissues can be fabricated in-situ from a bottom-up approach. Each layer may be tuned to have the desired geometry and composition. Any additional layer may be deposited on top of the mentioned layered.

The application of in-situ bioprinting using the present device and strategy is not limited to topical and skin surgeries. Any tissue adhesive, or more complex geometries can be applied and implemented on internal organs as well in a surgery.

The application of the present printer is not restricted to the mentioned cell types. Other cell types like IPS derived cells, and other micro-organisms like bacteria, and fungi can be printed in-situ and organized within hydrogel sheets using this method. The load can have emulsions of microparticles, gold and silver nanoparticles, microbubbles, graphite, conductive inks, and any other mixture and suspension of the mentioned materials can also be printed using this method. The application of this method is not limited to biomaterials. Beauty supplies, tattoos, creams, topical coverings, motion and flex sensors, conductive inks, among others, can be patterned and printed in-situ.

The use of the present tissue printer in both in-vitro and in-vivo studies will now be described with the following non-limiting examples In-Vitro and In-Vivo Studies Particularly, both in-vitro and in-vivo studies were performed using the handheld embodiment of the tissue printer. For the former, the inventors coated the bottom surface of a dish or multi-well plate with a hydrogel layer (e.g., agarose or gelatin) and hydrated it with the cross-linker solution. The hydrophilic and biologically inert surface ensures printing consistency and provides the bioprinted skin tissues with mechanical support during culture. After the handheld tissue printer deposited the bioink layer, gelation was induced by diffusive release of cross-linker from below as well as the cross-linker layer co-extruded at the top. Depending on the application, the bioprinted skin substitutes may be cultured in the same dish, or cut and transferred after 2-10 min (depending on the sheet thickness) to another dish, multi-well plate, transwell insert, or to a wound site. As a case study that serves to illustrate the compatibility of the approach with direct deposition in-vivo, we deposited the bio-ink layer directly onto a wound bed.

Methods

Preparation of Agarose Substrate

A solution of 2% agarose (UltraPure Agarose, 16500100, Invitrogen) in de-ionized (DI) water was prepared by microwave heating. The solution was allowed to cool to 60° C. prior to being poured into sterile square petri dishes (model Z692344, Sigma Aldrich) and resulted in a 3 mm thick gel. The gel solidified at room temperature for 30 min prior to use. For preparation of sodium alginate-based sheets, 50 mM calcium chloride (CCL302, BioShop) was added to the solution prior to microwave treatment. For printing of fibrin-based sheets, 2 ml of 50 IU thrombin (T4648, Sigma Aldrich) in PBS (Ser. No. 10/010,023, Gibco) was pipetted to hydrate the agarose substrate before extrusion.

Bioink Preparation

Bioinks with three different compositions were prepared. For alginate-collagen sheets, sodium alginate (Pronva UPLVG, Novamatrix) was dissolved in DMEM (11965-084, Gibco) and 20 mM HEPES (Ser. No. 15/630,080, Gibco) and filtered using 0.1 μm syringe microfilter (Millipore). Collagen type 1 (rat tail, 354249, Corning) was balanced to a pH of 7 using 1 M NaOH in PBS. The two stock solutions were mixed to obtain a final concentration of 5 mg/ml collagen and 2% alginate. The solution was kept on ice prior to use. To prepare the bioink for the dermal layer 5% fibrinogen (F8630, Sigma) was dissolved at 37° C. in PBS with mild agitation for 2 h. 1% HA (sodium hyaluronate Pharma Grade 80, Novamatrix) was dissolved in PBS. The solutions were mixed at a ratio of 1:1 and then filtered. Collagen type 1 solution was balanced with NaOH to a pH of 7 and mixed with the filtered Fibrin/HA solution to obtain a final concentration of 1.25% Fibrinogen, 0.25% HA and 0.25% Collagen. The solution was kept on ice prior to use. The bioink for the epidermal layer was prepared with a final concentration of 2.5% fibrinogen and 0.25% HA.

For printing the fibrin based sheets, a layer of 50 IU thrombin was co-extrusion above the fibrinogen based dermal and epidermal bioinks. The rapid enzymatic reaction between fibrinogen and thrombin is mass transfer limited in the considered case. The selected approach allowed the formation of sheets on the site of the deposition which solidified at time scales between tens of seconds and several minutes, depending on the thrombin concentration and sheet thickness, t. The gelation time is directly dependent on the sheet thickness. For the dermal bioink consisting of a mixture of collagen and fibrinogen, the gelation of fibrinogen occurs first and is induced by the diffusion of thrombin. As a result the sheet thickness and composition are maintained while the slower thermally induced gelation of neutral pH collagen progresses.

The alginate-based sheets were prepared by co-extrusion of 10 mM calcium chloride above the biopolymer layer. Similarly, rapid ionic cross-linking of alginate preceded the slower thermal gelation of neutral pH collagen. After the gelation of the sheet was completed, alginate was removed by incubating the sheet in 1 mg/ml alginate lyase (A1603, Sigma) for 30 min.

Physical Characterization of Deposited Skin Substitutes

Physical characterization of the deposited sheets included sheet thickness and contact angle measurements, the measurement of spot and stripe sizes, tensile strength. The microstructure was characterized by scanning electron microscopy (SEM) for $n \geq 3$ samples.

Sheet Thickness

Figure 21:
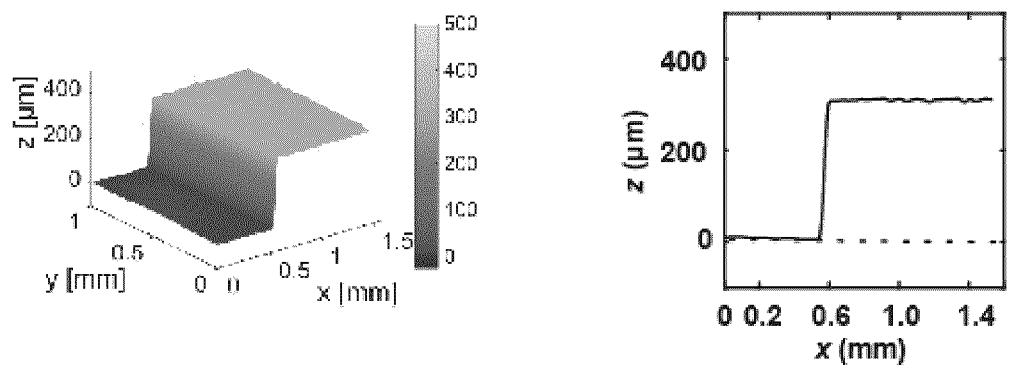
FIG. 21. Representative optical profilometry image and cross-sectional view of t=0.3 mm sheet with obtained with handheld bioprinter embodiment 1, W=14 mm.
Figure 23:
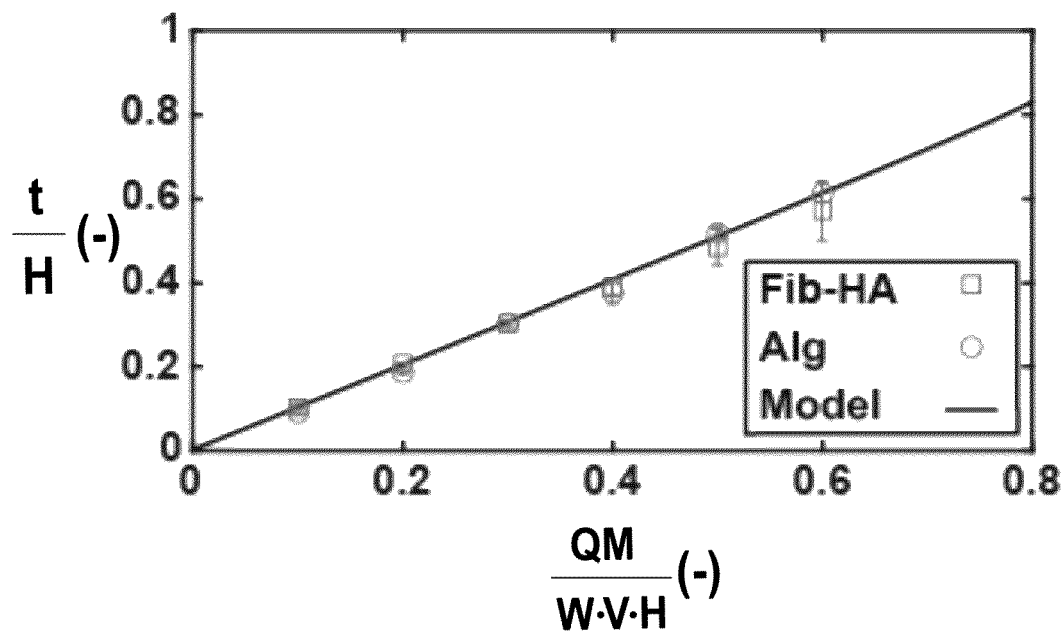
FIG. 23. Measurement and model predictions for dimensionless sheet thickness, t*=t/H, as function of dimensionless biopolymer flow rate, QM*=QM/(WVH). Measurements obtained for handheld bioprinter embodiment 1.

The precursor solutions were mixed with 5% 0.2 μm diameter fluorescent microparticles (FP-0245-2 or FP-0256-2, Spherotech). The sheets were transferred onto microscope cover slides and imaged using a confocal microscope (model A1, Nikon) using a digital camera (model Retiga 2000R Fast 1394, Q Imaging). The images were analyzed using the ImageJ software. Thickness of 5 random points on each sample were averaged and a total of 5 random points were selected for each experimental condition. The sheet thickness was also determined using an optical profilometer (model Contour GT-K, Bruker). The sheets were sectioned while attached to the agarose substrate and transferred to the profilometer stage. The Vision64 software program was used to analyze and export the sheet thickness data. 3D profile data were then imported into MatLab. Reported thickness data correspond to local averages over a 0.5×0.5 mm² region of interest for each of the 5 randomly selected points on a sample. For each experimental condition, n=3 sheets were measured. FIG. 21 shows the measurement data. The flow rates that are used in this research for obtaining various thicknesses are derived from the model shown in FIG. 22. FIG. 23 shows measurement data for sheets prepared in different biopolymers compared with model predictions.

Contact Angle

We deposited sheets of alginate-collagen, fibrin-collagen and fibrin on agarose that were 10 mm long, 14 mm wide and 250 μm thick. In a parallel test, a comparable volume of the fibrin-HA bioink, 35 μL, was pipetted onto an agarose substrate and allowed to gel under saturated atmosphere (humidity 100%) within an incubator. The shapes of the deposited droplet and the sheet obtained using the handheld Skin Printer were photographed with a Drop Shape Analyzer (DSA30, KRUSS) at 2° inclination angle with respect to the substrate plane.

Turbidity Measurements

Figure 24:
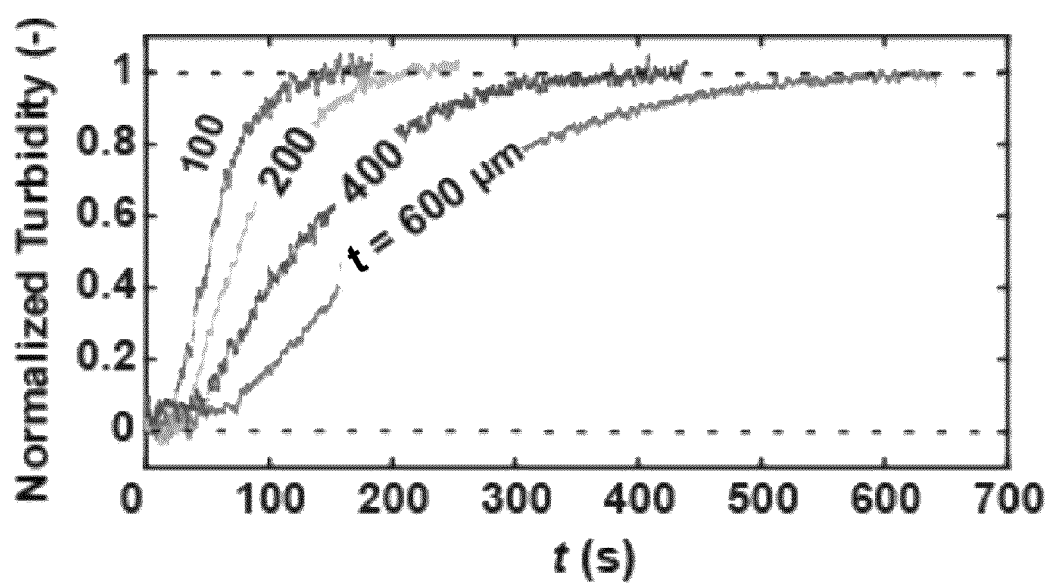
FIG. 24. Characterization of gelation kinetics based on measurement of time-dependent changes in normalized turbidity of fibrin-based sheets with different thicknesses. Measurements obtained for handheld bioprinter embodiment 1.

In-situ turbidity measurements (IST) were conducted as follows. The beam of a continuous wave argon-ion laser ($\lambda$=488 nm, 200 mW, Spectra-Physics) was expanded ten times, guided with a mirror to vertically penetrate an optically clear measurement section and collected by an amplified photodetector (Thorlabs). Sheet deposition experiments were conducted on top of the measurement section, within an agarose coated petri dish. The absorbance of the petri dish and the agarose was found to be negligible. The handheld tissue printer was used to deposit sheets of fibrin-HA bioink with different thicknesses (100, 200, 400, and 600 μm) on top of the agarose layer at a deposition speed of V=4 mm/s. The voltage signal (U) generated from the transmitted laser light was acquired using an oscilloscope (Tektronix). To quantify IST, the recorded voltage on the oscilloscope was converted to absorbance by $A=-\log(U/U_0)=\alpha l$ where $U_0$ is the voltage read by the oscilloscope in the absence of a sheet, $\alpha$ is the absorption coefficient ($cm^{-1}$), l is the length of the light path equivalent to the sheet thickness, t. The turbidity, $\tau=(A/l)\ln 10$, was plotted over time as shown in FIG. 24. Turbidity measurements were recorded approximately 3s after the cartridge of the handheld tissue printer translated out of the light path.

Stripe and Spot Sizes

Two syringes of bioink were prepared and loaded onto the handheld tissue printer. A secondary biopolymer solution contained fluorescent Nile red microparticles (FCM-1056-2, Spherotech) and a primary biopolymer solution without fluorescent particles. The cross-linker solution was supplied with an external syringe pump (PHD 2000, Harvard Apparatus). Stripe patterned sheets were deposited using a dedicated microfluidic cartridge design. Its microchannel configuration allowed the formation of biopolymeric sheets where stripes or spots of the secondary biopolymer were periodically incorporated within the primary biopolymer solution. Varying the flow rate ratio of the secondary and primary solutions allowed the relative stripe widths to be controllably varied. Upon gelation, stripe-patterned sheets were transferred onto cover slides for confocal microscopy. The reported stripe width represents an ensemble average over the individual stripe widths measured at 3 points (top, middle, bottom), over all stripes. ImageJ was used for image analysis.

In order to obtain spotted patterns, another dedicated microfluidic cartridge design was prepared that supplied the secondary biopolymer solution from an on-chip reservoir (i.e., instead of a syringe pump). After priming the reservoir with the fluorescently labelled secondary biopolymer solution, a square-wave pressure signal was applied to the air-filled reservoir headspace. A solenoid valve (LHL series, Lee Company) controlled with an Arduino Mega microcontroller to change the frequency and duty cycle of the pressure signal. Spot size and volume were controlled by adjusting the upper pressure level, and the valve open times.

Tensile Properties

Figure 26:
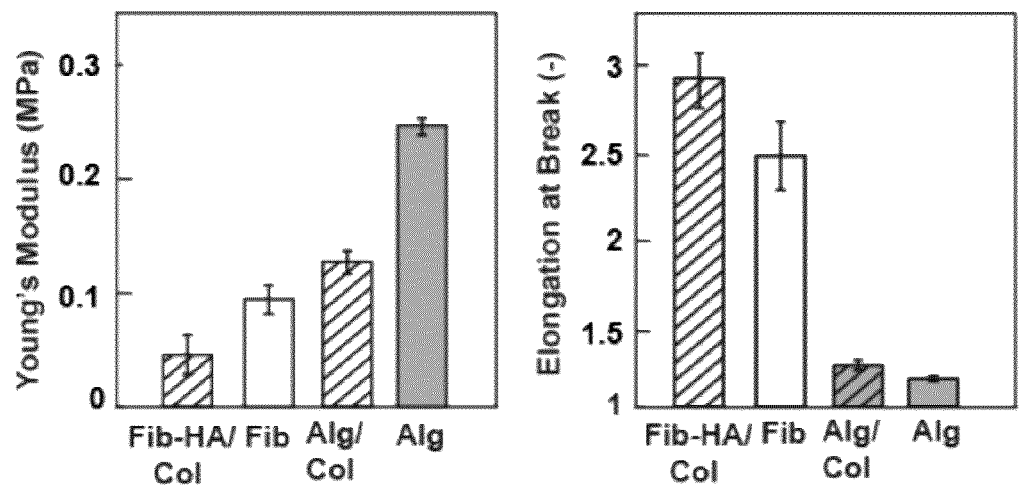
FIG. 26. Measured Young's moduli (left) and elongations at break (right) for sheets consisting of fibrin-HA/Col, fibrin-HA, collagen-alginate and alginate. Measurements performed for sheets prepared with handheld bioprinter embodiment 1.

Uniaxial tensile measurements of the collagen and agarose sheets were measured using a custom tensile tester based on the design described by Tremblay et al[32]. The hydrated sample sheets of approximately 10 mm length were on two opposing sides held by custom C-shaped clamps with sandpaper attached to clamp surfaces. Clamps were positioned in the vertical direction, z, using manual translation stages (MT1B, Thorlabs). Motion along the direction of pulling, x, was controlled by a linear voice coil motor (LVCM-051-051-01, MotiCont) on a ball bearing slide (37-360, Edmund Optics). A motion controller (DMC-4143, Galil) was addressed using a custom LabVIEW software program and controlled the displacement of the voice coil motors in feedback mode with an optical encoder (MII 1610S-40, Celera Motion) signal. Samples were pulled at a speed of 0.01 mm/s and displaced until fracture. A Load cell (Model 31 Low, Honeywell) measured the force at a given displacement. A DAQ Card (USB-1208LS, Measurement Computing) and amplifier (Model UV-10, Honeywell) were used to transfer the signal from the load cell to the motion controller. Sample length and width were evaluated using Zeiss and Nikon Ti inverted microscopes, to calculate the cross-sectional area. The latter in combination with the motor position and the load-cell corrected force resulted in a stress-strain curve. A linear regression was fitted to the elastic region to calculate the Young's modulus of each sample. FIG. 26 shows results from tensile measurements.

Microstructure

Figure 25:
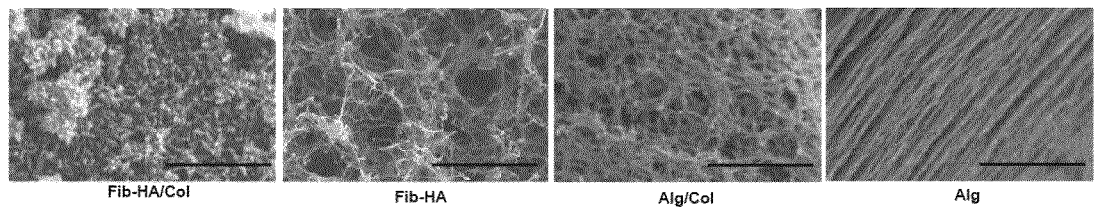
FIG. 25. Microstructure characterization of printed sheets with different biopolymer compositions using scanning electron microscopy. Measurements performed for sheets prepared with handheld bioprinter embodiment 1.

Alginate, collagen, and fibrin based biomaterials were fixated for one hour with Karnovsky's style fixative in Sorensen's buffer at room temperature, then dehydrated in serial ethanol washes with solutions containing between 30% and 100% ethanol. Samples were then dried using a critical point dryer. Gold was sputtered, prior to imaging on a scanning electron microscope (S-3400N, Hitachi) using an accelerating voltage of 30 kV. FIG. 25 shows electron micrographs of printed biomaterial sheets with different compositions.

In-Vitro Characterization

Cell Sources:

HDFa were obtained from healthy human normal skin after surgery. Cells were cultured in growth medium (DMEM, 10% fetal bovine serum (FBS) and 1% antibiotic/antimycotic (Ab/Am) until near confluency and split into further passages by treatment with 0.05% trypsin-EDTA treatment. Human umbilical epidermal keratinocytes (C-011-5C, Gibco Invitrogen) were cultured according to company instructions in EpiLife Medium with 1% HKGS and 1% Ab/Am and trypsinized using the same trypsin-EDTA solution as for fibroblasts. Cell passages 3-5 were used throughout this study.

Deposition of Cell-Populated Skin Substitutes

For in vitro preparation of skin substitutes, the dermal bioink contained $0.5 \cdot 10^6$ human primary fibroblasts and then deposited as a $\delta_D=500$ µm thickness sheet on agarose. The sheet was incubated at 37° C. for 20 min to allow for complete thermal gelation of collagen. The epidermal bioink contained $1.5 \cdot 10^6$ human primary keratinocytes. The epidermal layer was printed sequentially on top of the dermal layer with a thickness $t_E=200$ µm. Depending on the study, different patterns of epidermal layer (homogeneous or striped) were deposited on top of the dermal layer. The sheets were then immersed in culture media (EpiLife Medium, with 60 µM calcium, Gibco™). The sheets were the detached from the agarose substrate, sectioned to desired sizes and cultured in multiwell plates.

Cell Viability

Human dermal fibroblasts and keratinocytes were cultured in collagen/fibrin and fibrin gels, respectively, for three days in EpiLife media with HKGS growth supplement and 1% penicillin-streptomycin. Cells were then stained using calcein and ethidium homodimer for analysis of live versus dead cells, in addition to Hoechst as a cell nucleus stain. Confocal images of cells in biomaterials in individual 96-well plates were taken at 4× and 10× magnification with three biological replicates. Percentage viability was calculated by using the ImageJ software to count the number of cells stained positive for either calcein or ethidium homodimer and comparing them with the total number of cells as indicated using Hoechst nuclear stain as shown in FIG. 28a,b.

Cell Density

Human dermal fibroblasts and keratinocytes were cultured for three days using the previously described method. Cell density was observed by staining the cells with Hoechst, imaging with confocal microscopy, and automatically calculating the total number of cells using ImageJ software.

Immunohistochemistry

Cells in sheets were fixed with 4% paraformaldehyde in HBSS for 1 h at room temperature then washed with HBSS. They were permeabilized with 0.5% Triton X-100 in HBSS for 30 min at room temperature and then washed with HBSS. Cells were blocked with block buffer (1% BSA in 0.25% Triton X-100 in HBSS) for 1 hour. Antibodies were diluted in block buffer and incubated overnight at 4° C. Primary antibodies included fluorescein phalloidin (Life Technologies) and cytokeratin 14 (Santa Cruz Biotechnology). In cases where only phalloidin staining was performed, the mounting step was performed next. With keratinocytes, samples were washed with HBSS then incubated with secondary Alexa Fluor antibodies (Life Technologies). After 3 washes, slides were mounted with Vectashield mounting medium with DAPI (Vector Laboratories). Images were taken on Apotome Axiovert whole field fluorescence or Observer Z1 spinning disk confocal microscope (both Zeiss).

Histology

Tissue specimens were fixed in 10% buffered formalin overnight at 4° C., stored in 70% ethanol and embedded in paraffin. Specimens were cut into 5 µm sections in the centre of the wound. Trichrome reagents were obtained from EMS (Hatfield) unless otherwise stated. Briefly, paraffin embedded slides were deparaffinized with citrosol, followed by rehydration through grades of ethanol to water. Slides were placed in Bouin's solution for 1 h at 60° C. and washed in water. Hematoxylin (Sigma) and Biebrich scarlet-acid fuchsin solution were stained for 10 min each, respectively with washes in between. Slides were differentiated in phosphomolybdic-tungstic acid for 15 min, and transferred to aniline blue for 5 min. Slides were rinsed and differentiated in 1% acetic acid for 2 min. Slides were dehydrated through 95% ethanol and absolute ethanol followed by clearing in citrosol. Slides were mounted with SHUR/Mount xylene-based liquid mounting medium (Triangle Biomedical Sciences). Images were acquired using a light microscope (Leica DM 2000LED).

For immunohistochemistry staining, paraffin embedded skin tissue slides were deparaffinized with citrosol followed by rehydration. Antigen decloaker (1×, Biocare) was added to the slides in a preheated decloaking chamber for 4 minutes at 110° C. Samples were blocked with 3% $H_2O_2$ for 10 min, then washed with washing buffer (0.05 M Tris-HCl, 0.15 M NaCl, 0.05% Tween 20 in DI water). Primary antibody was diluted in PBS and incubated at room temperature for 1 h. Primary antibody used was cytokeratin 14 (Santa Cruz Biotechnology). Next, slides were incubated for 15 min first with goat-on-rodent probe (Biocare Medical), and secondly with goat-on-rodent HRP-polymer. The beta-zoid DAB chromogen kit (Biocare Medical) was added for 5-10 min and the reaction was terminated with running water. Nuclear staining was done with hematoxylin for 30 s, followed by differentiation with 3 dips in 1.5% acid alcohol and bluing in 0.1% sodium bicarbonate for 10 s. Sections were dehydrated through 95% and absolute ethanol to citrosol and mounted with SHUR/Mount as previously described. Images were acquired using LeicaDM 2000LED light microscope.

Sheet Homogeneity and Uniformity.

FIG. 20 shows a bright field image of a t=300 µm sheet produced with the Skin Printer (right) in comparison with manually pipetted hydrogel precursor (left). Both images were taken at a 4° angle against the flat surface that was coated with a hydrated agarose layer. The pipetted hydrogel forms a dome-shaped, curved structure with a non-uniform thickness. Despite the small contact angle uniform spreading of the hydrogel is prevented by gelation of the hydrogel progressing from the perimeter. The sheets printed with the handheld Skin Printer, however, exhibit a consistent thickness t since the hydrogel precursor solution is uniformly distributed along the lateral direction, y, using parallel channels on the microfluidic cartridge and rapid gelation occurs uniformly in the sheet-normal direction. As a result, deposited t=300 μm thick and $w_0$=14 mm wide sheets have uniform thicknesses and sharp edges as shown in an optical profilometer scan (FIG. 20b). The nonuniformity which arises from the contact lines of the sheet to the agarose layer span only for less than 5% of the sheet width from each side. We next discuss the thickness t as a function of the printing parameters. We consider the laminar flow of a layered fluid between the two surfaces and apply lubrication theory[28]. Since $w_0/H>10$ we approximate the hydraulic diameter as 2H. We neglect the pressure gradient in z-direction and inertia forces. The continuity equation and the simplified momentum balance result in a single elliptic differential equation that describes the pressure gradient along the film. An analytical model is has been derived. The model considers the viscosities ($\mu_m$, $\mu_c$) and flow rates of the biopolymer and the cross-linker solutions (QC, QM) and predicts the biopolymer sheet thickness t (FIG. 22). The analytically predicted sheet thickness is in excellent agreement with values measured for bioprinted fibrin-based and alginate-based sheets (FIG. 23). Sheet thicknesses between t=100 μm and 600 μm can be reliably obtained using the considered microfluidic cartridge (H=1 mm). Printing thicker sheets would require a modified cartridge design (H>1 mm). In addition, larger sheet thicknesses increase diffusion length, ~t/2, diffusion time, ~$t^2$/4, and gelation time and decrease thickness uniformity. Consistent sheet deposition is achieved for the zero-pressure gradient case. For given viscosities $\mu_m$ and $\mu_c$, the flow rates QM and QC are selected such that the pressure is invariant along the direction of deposition $$\left(\frac{dP}{dx}=0\right),$$

and backflow or overflow are avoided.

The handheld tissue printer disclosed herein is compatible with different biopolymers. Here we show the compatibility with a polysaccharide-based biopolymer, (alginate) which uses ionic crosslinking, and a protein based biopolymer, (fibrin) with enzymatic reaction. In the alginate only and alginate-collagen cases, gelation is induced by ionic crosslinking with calcium chloride. Fibrin and fibrin-collagen sheets are prepared by an enzymatic reaction between fibrinogen precursors and thrombin. The compositions of the epidermal and dermal layer bioinks and cross-linker solutions are summarized in Table 1. Both bioink choices are highly biocompatible, biodegradable and do not require secondary washing steps prior to in-vitro culture or direct in-vivo implementation.

TABLE 1 formulation of the different biopolymer and crosslinker combinations used in this research.

| Bioink | Main Biopolymer | Secondary Biopolymer | pH | Media | Viscosity (at 1 $s^{-1}$ shear rate) | Crosslinker | Gelation rate |
|---|---|---|---|---|---|---|---|
| Polysaccharide based | Alginate 2% (w/v) | — | 7 | DMEM + 20 mM HEPES | 80 mPa · s | 50 mM Calcium Chloride in PBS | 200 μm/min |
| | Alginate 2% (w/v) | Collagen type 1 (2.5 mg/ml) | 7 (modified with NaOH) | DMEM + 20 mM HEPES | 108 mPa · s | 50 mM Calcium Chloride in PBS | 200 μm/min, 10-30 min thermal gelation |
| Protein based | Fibrinogen (20 mg/ml) | Hyaluronic acid 0.5% (w/v) | 7 | PBS or DMEM | 1.18 Pa · s | 50 IU Thrombin in PBS | FIG. 2e |
| | Fibrinogen (20 mg/ml) | Hyaluronic acid 0.5%, collagen type 1 (2.5 mg/ml) | 7 (modified with NaOH) | PBS or DMEM | 0.95 Pa · s | 50 IU Thrombin in PBS | FIG. 2e, 10-30 min thermal gelation |

Understanding the progress of sheet gelation is a crucial aspect of the application of handheld tissue printer. Gelation is initiated at the interface between the biopolymer and cross-linker layers and propagates throughout the thickness of the biopolymer to result in complete gelation of the sheet. For alginate-based sheets, ionic gelation is induced rapidly upon contact with calcium chloride co-delivered from above. The gelation of fibrin is a slower process. In order to retain the deposited sheet architecture, e.g., multi-layered or stripe-patterned sheets, while gelation occurs, we increased the viscosity of fibrin-based bioink by adding hyaluronic acid. We performed systematic turbidity measurements to assess the kinetics of gelation. FIG. 24 shows the turbidity measurement of the fibrin-HA sheets at different thicknesses that were varied between t=100 μm and 600 μm. Gelation was induced by inter-diffusion of thrombin from above (co-extruded) and below (diffusively released).

The ability to controllably deposit both polysaccharide-based (e.g., alginate) and protein-based materials (e.g., fibrin-collagen) and mixtures thereof allow us to select the biomaterial composition in light of favorable printing behavior, as well as cell attachment and function. FIG. 25 shows representative scanning electron microscopy (SEM) images of the microstructure of the four bioink compositions considered in this paper. FIG. 26 shows the Young's modulus and elongation at break of the deposited sheets. Alginate-based composites show higher Young's modulus, compared with fibrin-based sheets. The latter exhibit higher elasticity and 2.6 times higher elongation at break (constant strain).

Figure 27:
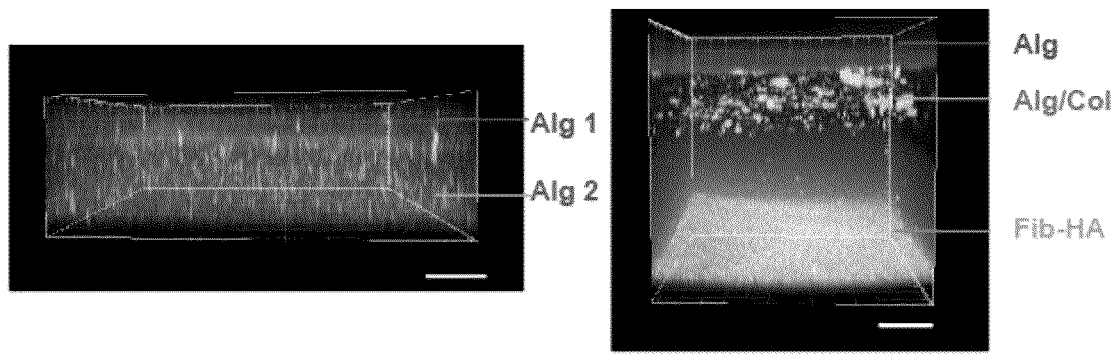
FIG. 27. Left: Confocal image of bi-layer sheet prepared by subsequent deposition of a 0.2 mm thickness alginate sheet with payload of green fluorescent microparticles (bottom layer), and a 0.1 mm thickness alginate sheet with red fluorescent microparticles (top layer). Right: Confocal image of three-layer sheet prepared by subsequent deposition of a 0.5 mm (bottom layer) fibrin-HA sheet with blue microparticles, a 0.2 mm (middle layer) alginate-collagen sheet with FITC-conjugated collagen and a 0.15 mm (top layer) alginate sheet with red microparticles. Scale bars 0.1 mm. Data obtained for sheets prepared with handheld bioprinter embodiment 1.
Figure 28:
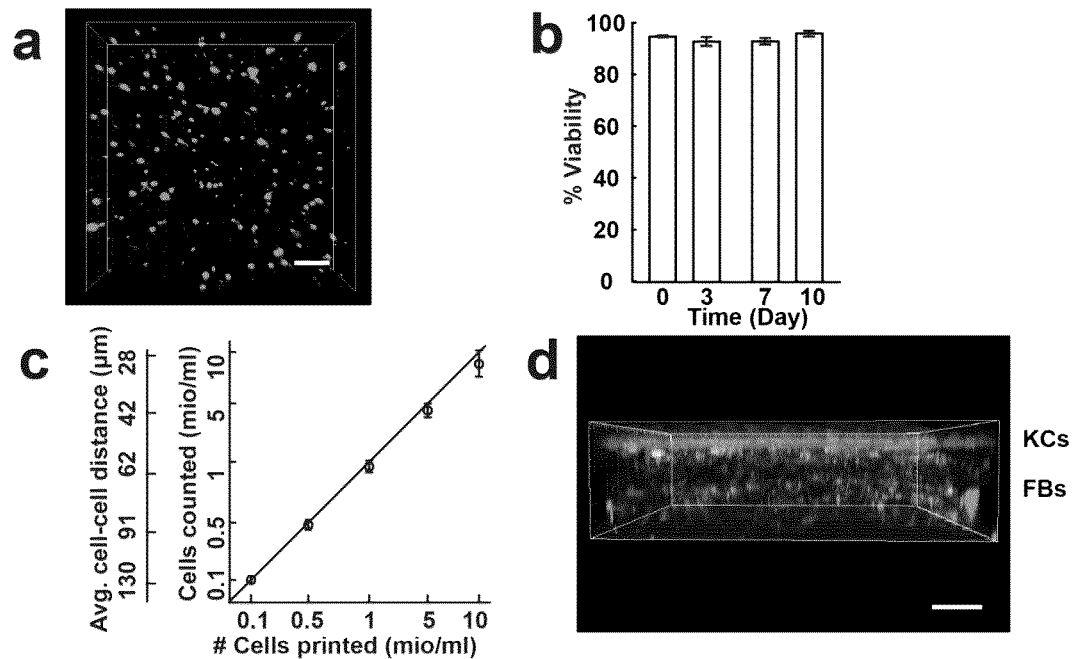
FIG. 28. (a) Homogenous printed sheet contains human dermal fibroblasts (FBs). Live cells indicated by calcein stain, and dead cells indicated by fluorescent ethidium homodimer-1. (b) Quantitative assessment of FB viability in printed fibrin/HA/collagen-I bioink with >90% cell viability during 10-day culture. (c) Various concentrations of cells were printed in bioink and quantified using Hoechst nuclear staining, showing no loss in total cell number due to printing. (d) Bilayer construct printed in stepwise fashion. Keratinocytes (k14 & phalloidin co-stain) printed on top of FBs (phalloidin) resembling bi-layered structure of skin. Data obtained for sheets prepared with handheld bioprinter embodiment 1.
Figure 29:
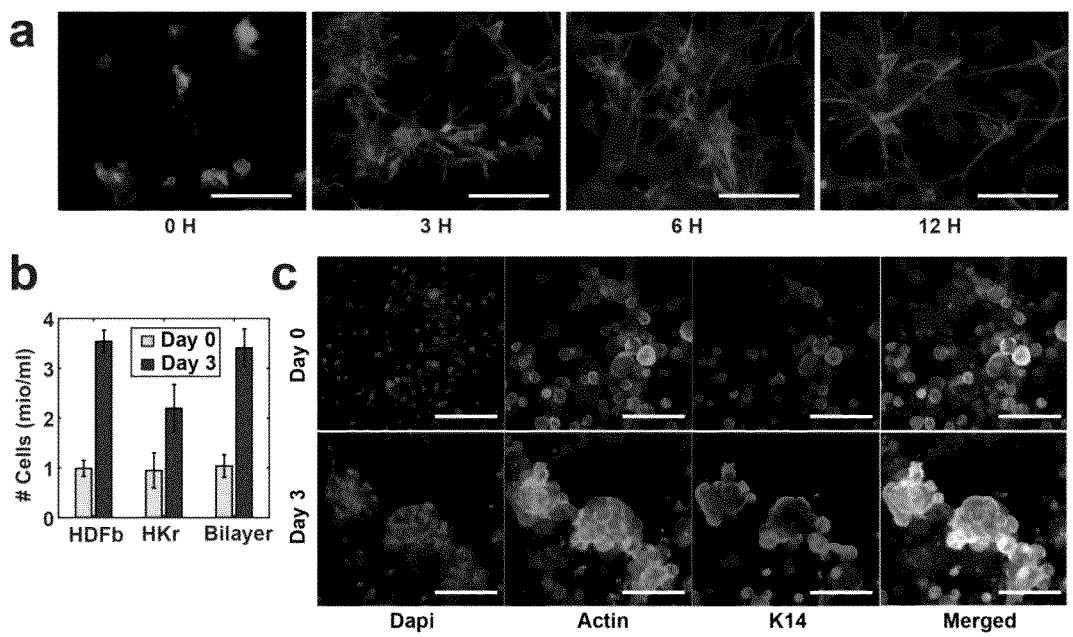
FIG. 29. (a) FBs printed within 1.25% fibrin/0.25% collagen/0.25% HA extracellular matrix material and stained with Hoechst and phalloidin shows attachment and elongation of cells during 12 hr. (b) Comparison between day 0 and day 3 of human keratinocytes (KCs) printed in fibrin gel using immunofluorescent staining for cell nucleus, actin, and keratin-14 indicating cell grouping and clustering by day 3. (c) Quantitative assessment of FB and KC cell numbers of over 3 days of culture. Scale bars: 0.1 mm (a, b). Data obtained for sheets prepared with handheld bioprinter embodiment 1.

To obtain multilayered sheets with controllable thicknesses, sheets can be consecutively deposited using the handheld Skin Printer. The stepwise approach enables the deposition of multilayered sheets with the matrix or the cellular composition varying in the vertical (z) direction. FIG. 27 shows a confocal micrograph of a sheet that was formed in three consecutive steps: First, a 500 μm layer of fibrin with a payload of 0.1 μm blue colored polystyrene particles were deposited. After 5 min, a mixture of alginate and FITC conjugated collagen type 1 was deposited on top of the first layer. After 30 min, the final 150 μm thick layer of alginate containing 0.2 μm Nile red particles was deposited.

Stripe and Spot Patterned Sheets

Figure 7:
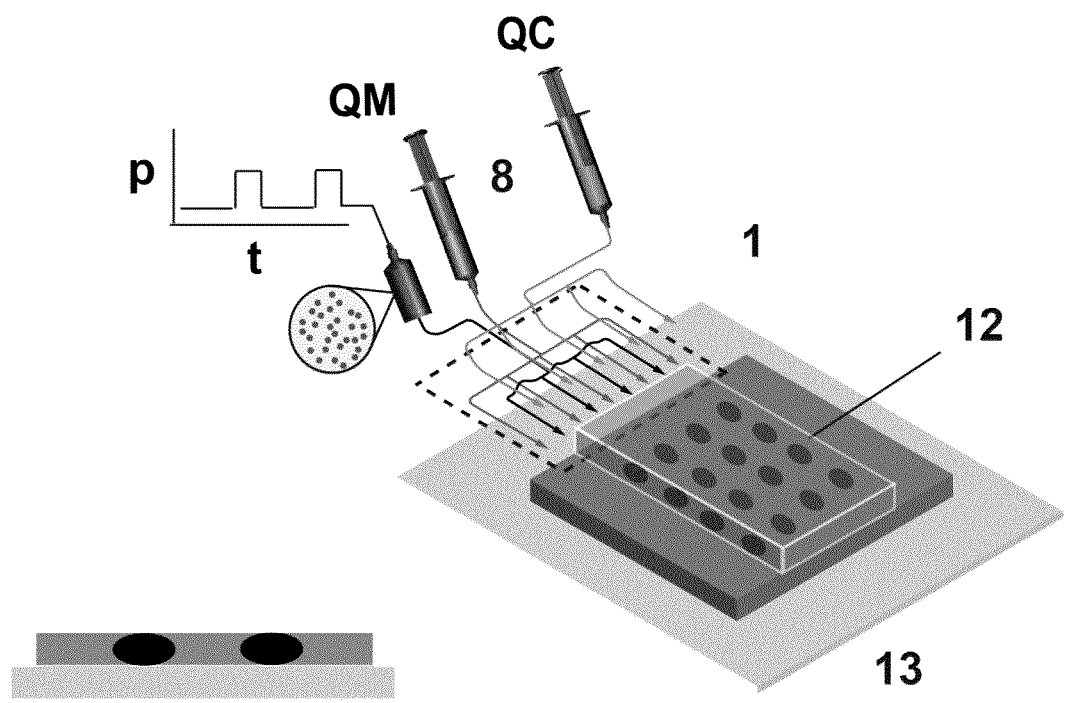
FIG. 7. Schematic illustration of spot patterned sheet formation.
Figure 8:
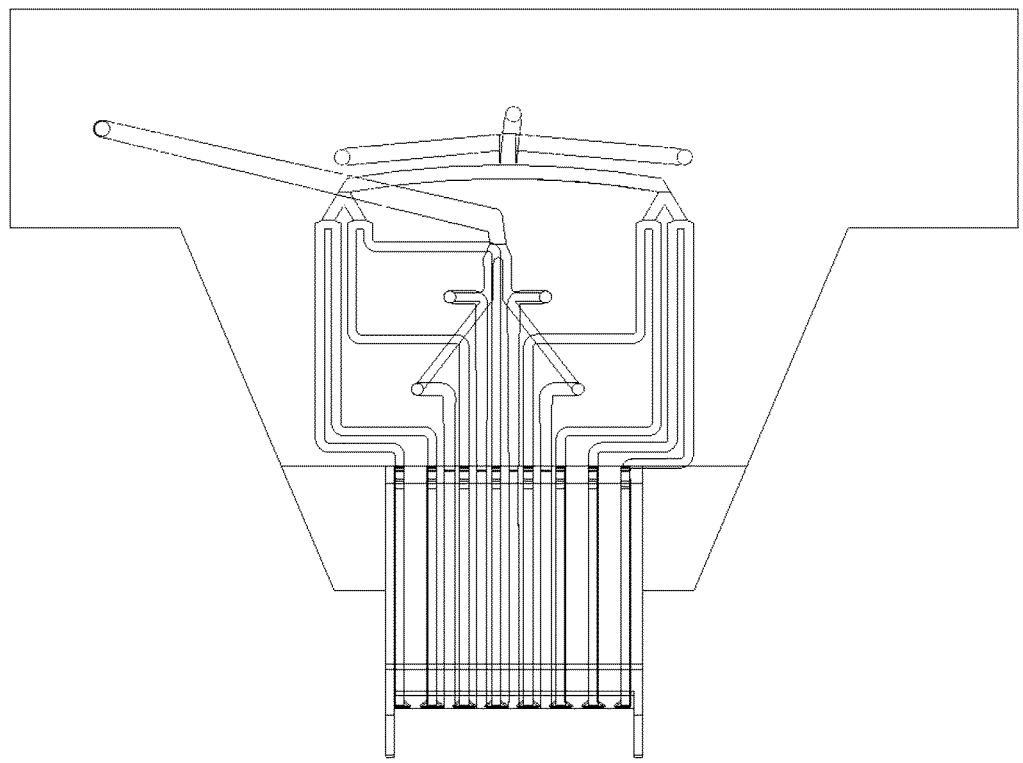
FIG. 8. Frontal view of microchannel network in printer head design in 3D printed embodiment.
Figure 9:
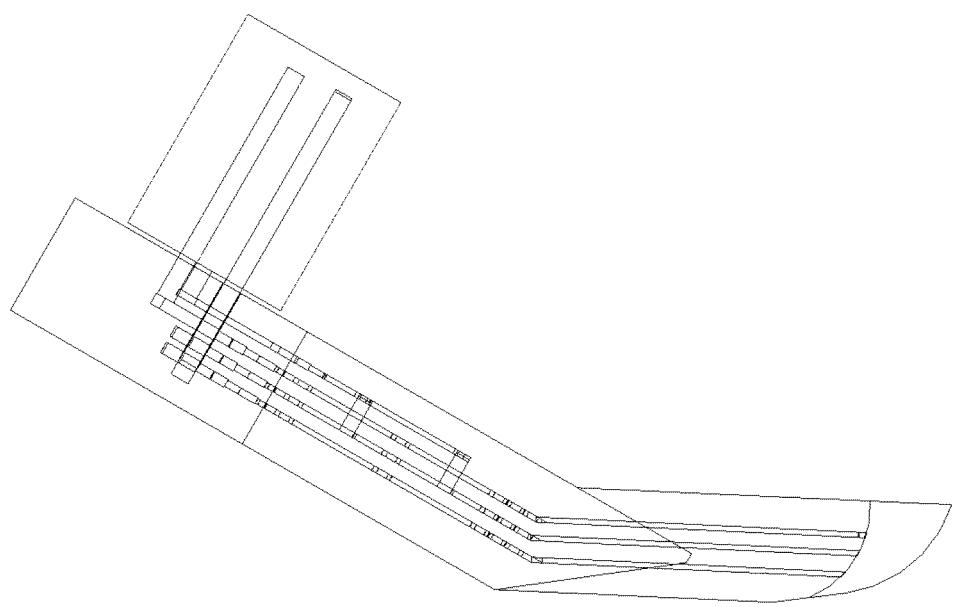
FIG. 9. Side view of printer head design.
Figure 10:
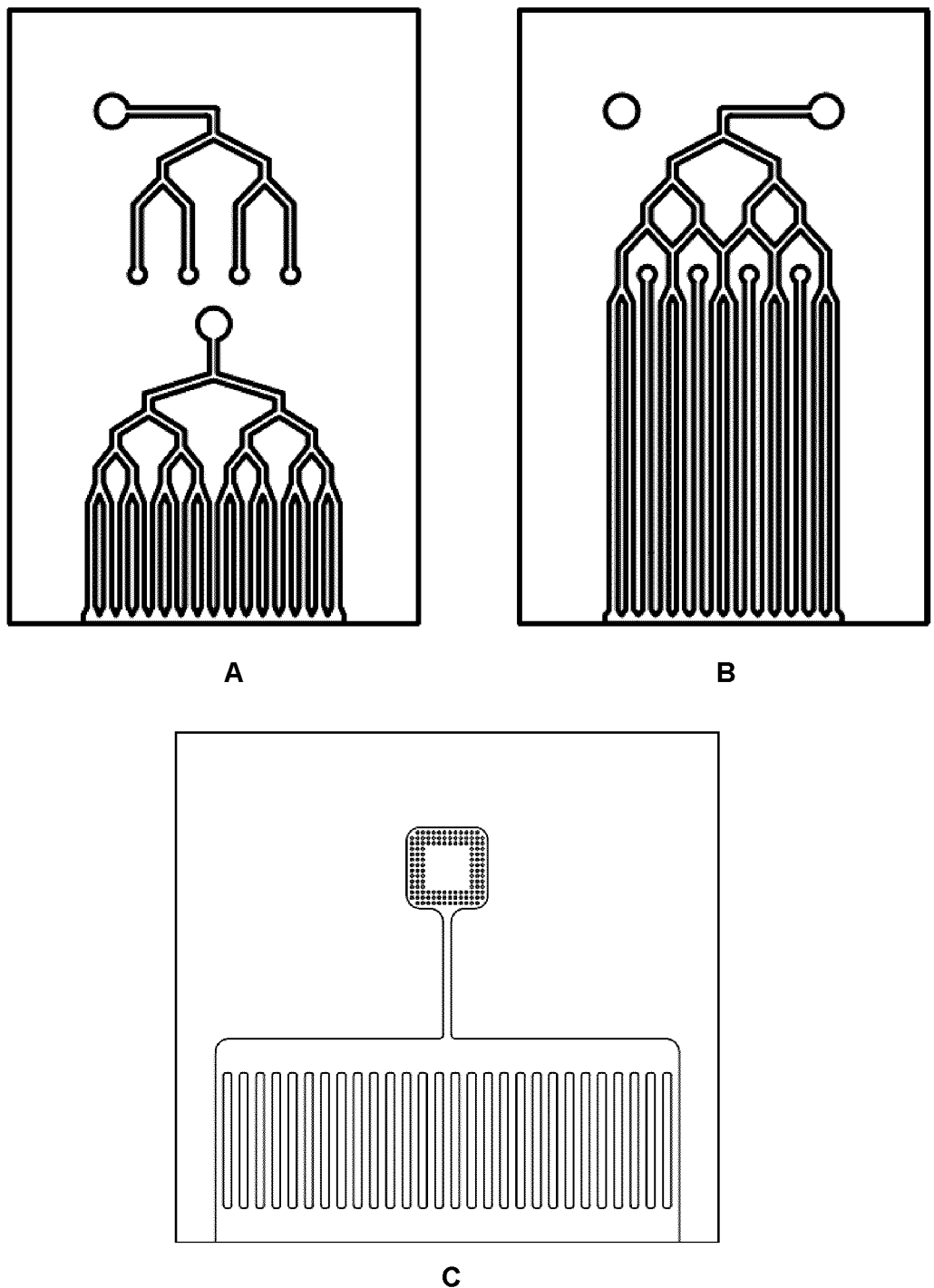
FIG. 10. Printer heads manufactured in thermoplastic substrates using thermal embossing or micro-injection molding.
Figure 11:
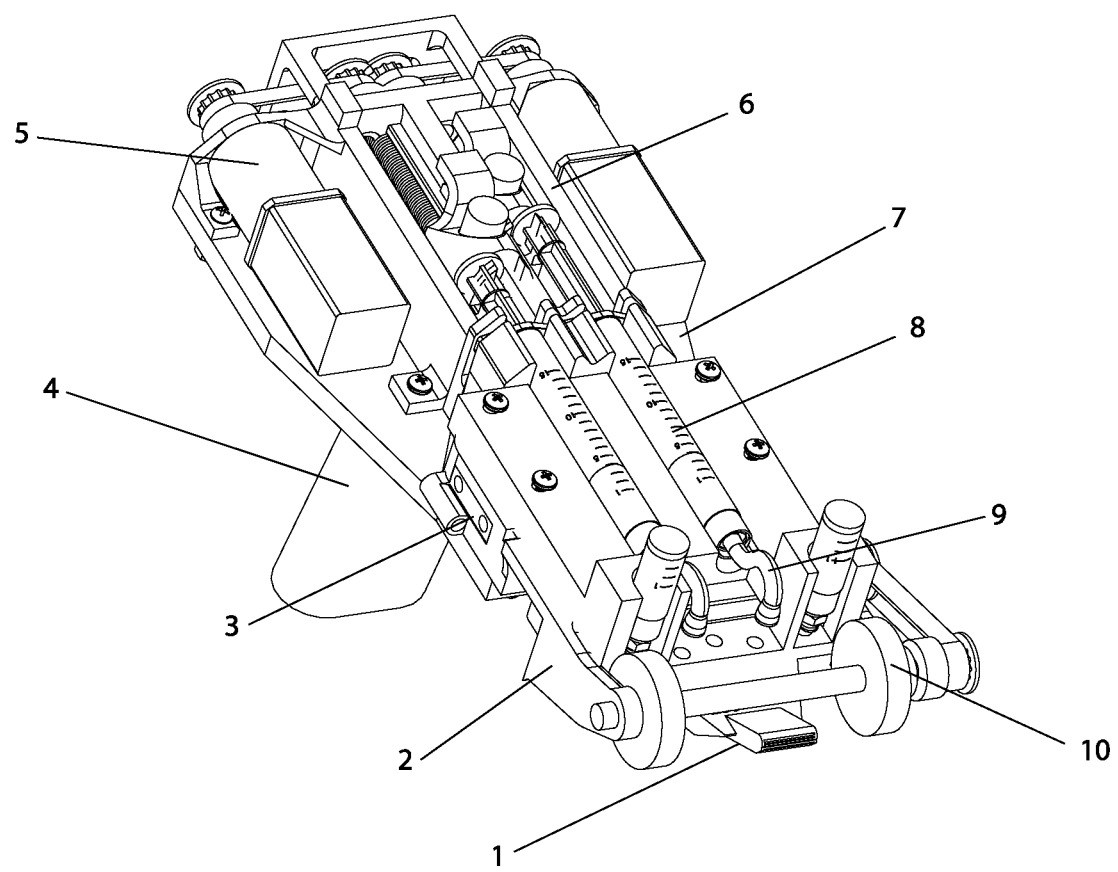
FIG. 11. Perspective view of handheld bioprinter in embodiment with rollers mounted on both sides of printer head.
Figure 12:
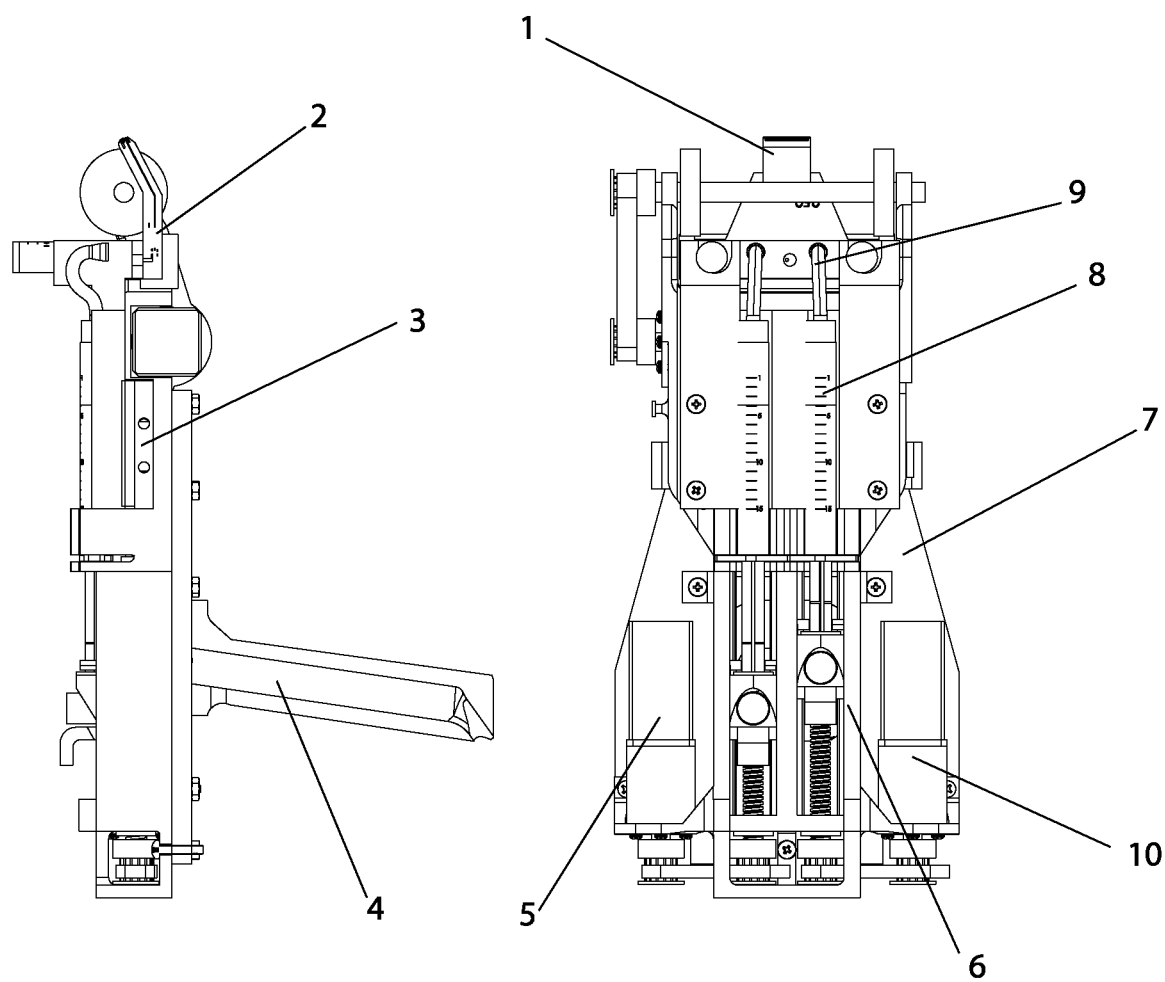
FIG. 12. Side and frontal views of handheld bioprinter in embodiment with rollers mounted on both sides of printer head.
Figure 13:
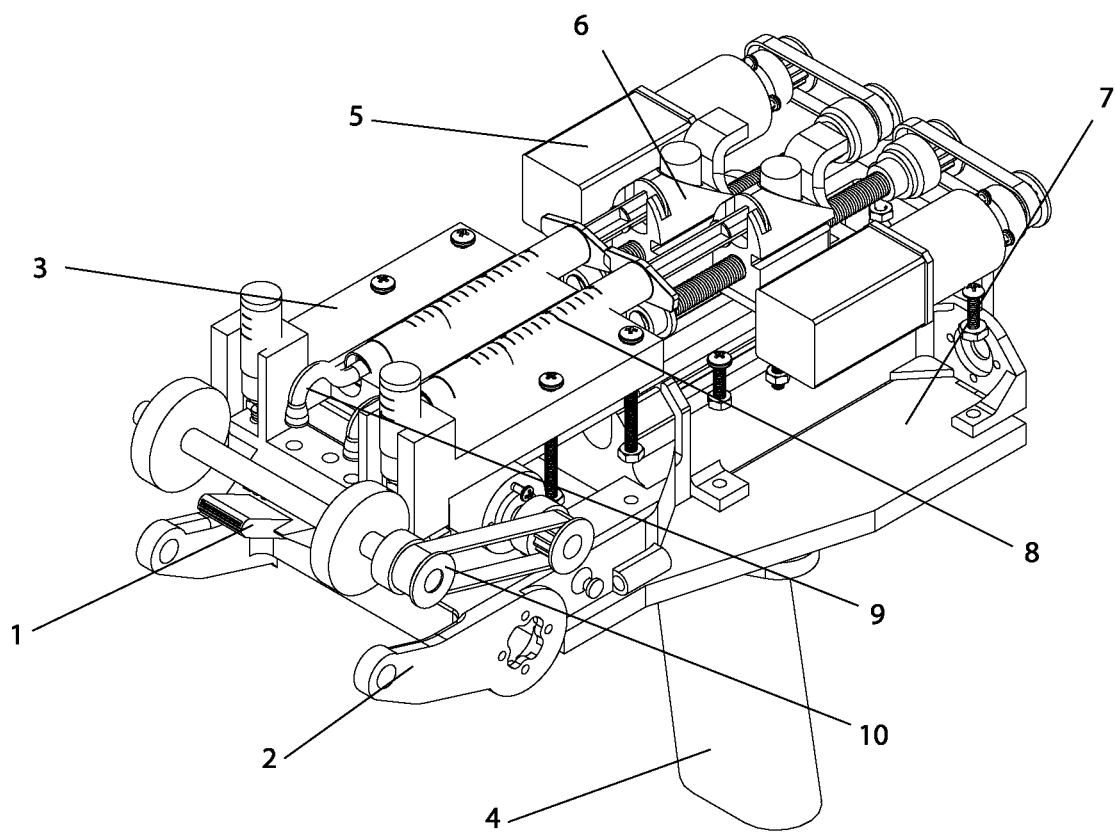
FIG. 13. Exploded view of handheld bioprinter in embodiment with rollers mounted on both sides of printer head.

The ability to control the sheet composition in both the printing direction (x) and the lateral direction (y) allows architected sheets to be produced without the need for moving parts. Respective biopolymer flow rates may be controlled using on board syringe pumps (FIG. 5 or FIG. 32a) to provide striped patterns or pressure control to provide spotted patterns (FIG. 7). Stripes narrower than the smallest feature size of the microfabricated cartridge were realized by utilizing hydrodynamic focusing[29]. Here, we demonstrate the incorporation of four stripes of a secondary biopolymer using an approach developed previously[30]. The relative stripe width, $w_{stripe}/w_0$, was altered by changing the flow rate ratio $Q_M/Q_C$ as shown in FIG. 32b,c. Spots were patterned instead of stripes when the secondary biopolymer solution was delivered from a pressurized well and a time-dependent head pressure was applied. Manipulating the frequency and the duty cycle of the square wave pressure signal can result in different spot sizes. The distance between subsequent spots is governed by valve off time as well as the flow rate of the primary biopolymer solution (FIG. 32d,e).

Handheld Tissue Printer In Vitro Studies

The handheld tissue printer is capable of depositing mammalian cells without impacting cell viability due to material choice and printing parameters. For in vitro experiments we selected a bioink composition including hyaluronic acid, fibrinogen, and type-I collagen. Gelation of the fibrinogen component is induced by the enzymatic activity of thrombin at neutral pH and room temperature. The addition of hyaluronic acid improved the viscosity and printability of the bioink without adversely impacting cell viability. Additionally, the printing approach is characterized by low shear rates (in the order of 1/s) that do not damage the cells. FIGS. 28a and 28b show that human dermal fibroblasts (HDFa) embedded in the fibrin-based biomaterial exhibited more than 90% viability based on a live/dead assay performed after 10 days in culture. We found, for five different concentrations of cells ranging from 0.1 to 10 million/ml, the original cell seeding density to be consistent with the cell density obtained at time zero after performing a Hoechst nuclear stain and confocal microscopy on printed sheets. No cell or biomaterials clumps or aggregates were observed immediately following printing, indicating that the delivered cells remain uniformly dispersed within the biomaterial.

FBs were mixed with fibrin-collagen-HA hydrogel precursor and printed using the handheld tissue printer. Bioprinted sheets were fixed and stained for nuclei and cytoskeleton at different time points post printing (0, 3, 6 and 12 hrs). The results suggest that the cells adapt to the 3D scaffold without impacting morphology, as they exhibit elongation and attachment within the first few hours of printing (FIG. 29a) comparable to standard cell culture conditions. Compared to acellular scaffolds such as Integra™ which relies on neighboring cells from the host to migrate and populate the delivered material, our approach utilizes a hydrogel pre-mixed with cells prior to deposition to facilitate cell survival and interaction with the surrounding microenvironment[31]. This can promote a faster dermal layer reconstruction in vivo compared to acellular matrices.

Figure 34:
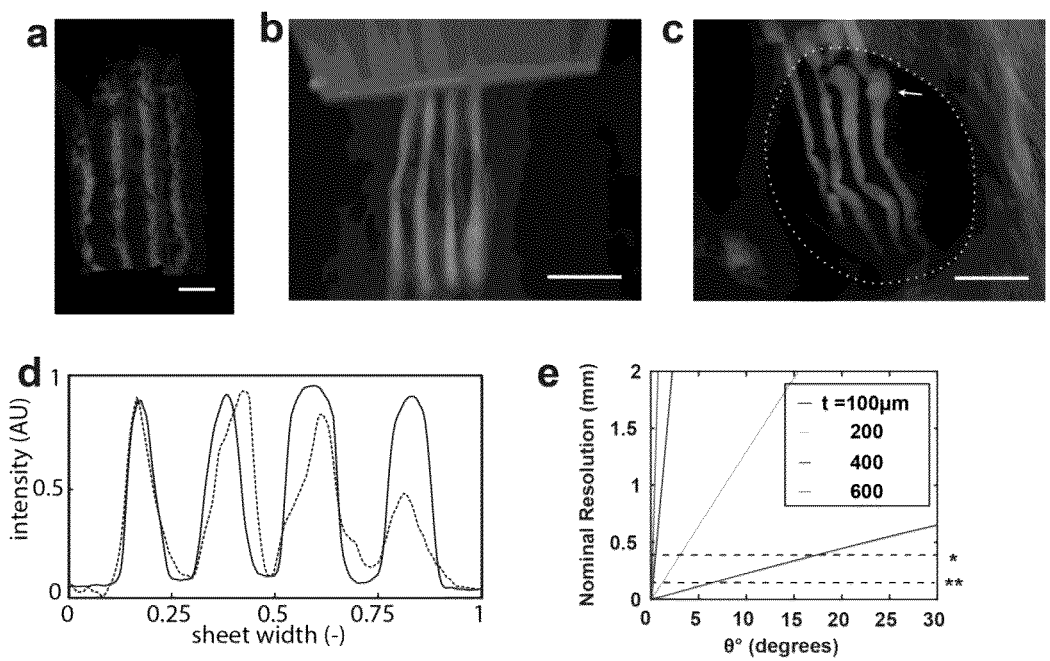
FIG. 34. (a) Stripe-patterned fibrin-HA sheet deposited on murine wound. (b). Fluorescent image of stripe-pattern deposition directly on murine excisional wound model. (c) Representative image of 4 stripes printed on 8 mm wound model. The dashed circle shows the wound edge. The arrow shows the initiation phase of the print until it reaches steady-state deposition. 1 μm green fluorescent microparticles used as label. (d) Normalized fluorescence intensity across in situ printed striped alginate sheet (solid line) and fibrin sheet (dashed line) (e) Estimate of nominal in-plane resolution for bioprinted fibrin-HA sheet deposited on flat surface with inclination angle. (*) Indicates width of channel delivering bioink stripes on microfluidic cartridge without flow focusing feature. (**) Indicates improved resolution achieved by 3D printed microfluidic cartridge with internal flow-focusing features. Scale bars 2 mm. Data obtained for sheets prepared with handheld bioprinter embodiment 1.

Keratinocytes (HEKa) are the essential cell component of the skin epidermal layer. Human KCs were mixed at a concentration of 1.25 million/ml and printed in a δ=200 μm layer using our Fibrin/HA bioink. Collagen-I materials were omitted from this composition to mimic the epidermal layer undergoing wound repair. By culturing the KC sheets over a three-day period, we demonstrated that printed keratinocytes exhibit normal morphology in this 3D matrix (FIG. 29c). On day 0, the cells are dispersed individually and homogenously distributed within the sheet. Within three days of 3D culture, the printed keratinocytes had a clustered morphology as visualized using z-stack confocal microscopy, suggesting normal epithelial activity. Additionally, we demonstrate that keratinocytes can also be organized in distinct patterns including stripes. The width and distance of the stripes can be governed by tuning the volumetric flow rate of the fluids and the design of the microfluidic printer head as illustrated in FIG. 34a. Here, four keratinocyte-containing stripes with $w_{stripe}$=500 μm were patterned in an 8 mm wide sheet and visualized using phalloidin staining.

To mimic the layered architecture of skin, a bi-layered sheet containing both keratinocytes and dermal fibroblasts was deposited (FIG. 28d). First, a 500 μm thick layer of human dermal fibroblasts at a concentration of $4 \times 10^5$ cells/ml in a collagen/fibrin matrix was deposited. Second, a 100 μm layer of keratinocytes embedded within a fibrin/HA matrix was deposited on top of the dermal layer. Immunostaining of the bi-layered construct revealed cell compartmentalization in a distinctive layered structure as illustrated with two distinct, yet connected, layers of cells. Cell numbers were quantified using a Hoechst nuclear stain and confocal microscopy to show that the total cell numbers increased over a three-day culture period, suggesting continued cell growth and proliferation (FIG. 29b).

Case Study for In Vivo Deposition Using Porcine Model

A male Yorkshire pig with a weight of 25 kg was exposed to excisional skin biopsy following the reviewed protocol by Sunnybrook animal care committee (AUP #: 16-600). The pig was housed in individual pens at room temperature and at a 12 hr light-dark cycle with food and water ad libitum at Sunnybrook Research Institute. Feeding and daily care was performed by the in-house animal staff and overseen by an assigned veterinarian. Standard diet and animal care standard operation procedures were obeyed. All animals were fasted for at least 6 hours before surgery and assessed daily using a standardized protocol elaborated together with the veterinarian. Pain medication was adjusted accordingly. After induction of anesthesia, hair was removed via electrical shaving followed by chemical depilation. The operation area was disinfected with povidone Iodine, skin excision in the previously marked areas was performed with a scalpel, the rest of the operation with a monopolar diathermy knife that was also used for hemostasis.

Porcine skin shares several characteristics of human skin, which makes it an ideal model for evaluating the feasibility of utilizing tissue printer in a clinically relevant setting. We deposited onto 20 mm×40 mm full-thickness excisional skin wounds and compared with the contralateral wound which did not receive any material (control, n=4). Wounds were marked on the back of the animal before the operation and full-thickness excisional wounds were inflicted. After the excision, the wounds were covered by direct deposition of a 300 µm fibrin-HA sheet (FIG. 30a-d), or nothing as a control. Bleeding stopped after approximately 5 min in the wounds covered by the wound-adhesive sheets while control wounds achieved hemostasis after tens of minutes.

Figure 31:
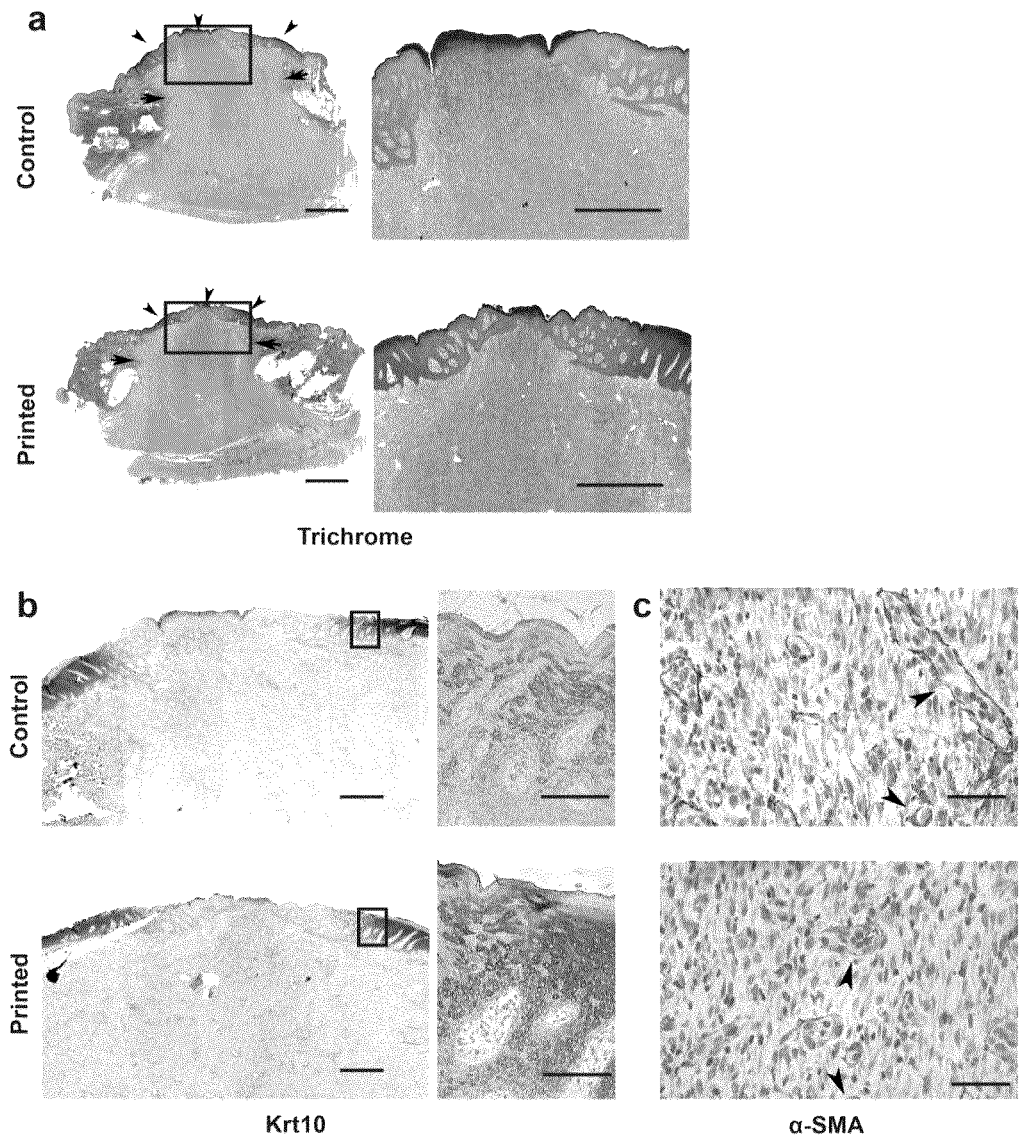
FIG. 31. (a) Trichrome staining indicates extent of granulation tissue formation and reepithelialization. Arrows in (a) indicate border between newly formed granulation tissue and intact skin. Arrowheads mark epithelialized area. Arrowhead at the center of treated wound shows complete re-epithelializion, while central arrowhead in control wound shows non re-epithelialized zone at wound center. (b) Keratin 10 staining is showing comparable extent of differentiated keratinocytes. At the corner of the Printed wounds more keratin positive cells were observed, supporting the notion that printed material fibrin-HA sheets likely enhance wound healing. (c) α-SMA staining reveals comparable number of positive cells in both printed and control wounds. Scale bars: 1 mm(a right, b left), 0.1 mm (b right), and 0.05 mm (c). Data obtained for sheets prepared with handheld bioprinter embodiment 1.

Microscopic analysis of the harvested healed wounds (sacrificed on day 20) revealed that both treated and control wounds formed a complete granulation tissue (FIG. 31) and the level of collagen deposition and cellularity of both treated and control wounds are comparable. Out of 4 control wounds, only 1 of them showed a complete re-epithelialization while 3 out of 4 treated wounds had a complete re-epithelialization (non-significant parametric test). To further evaluate and compare the wound healing characteristics, the healed wounds were stained with alpha-smooth muscle actin (α-SMA) and Keratin 10 (K10) antibodies. α-SMA is transiently expressed by myofibroblasts during skin healing and serves as a marker to evaluate the progression of skin healing.

The present data do not show a significant difference between treated wounds compared with the control wounds. Stains for K10, a marker of differentiation of cells in the epidermal layer, did not suggest a significant difference between the extents of differentiated cells in treated wounds in comparison with the control. The in-vivo results illustrate that the in-situ deposition of skin substitutes provides a non-detrimental hemostatic barrier immediately after application, and does not impede normal re-epithelization and wound contraction.

As noted above, at the end of the experiment after 20 days, the swine was euthanized and the wounds/scars were excised, fixed in formaldehyde and send for histological preparation. All tissue for staining was embedded in paraffin, cut into 5 µm thick slices and placed on standard glass slides for trichrome staining and immunohistochemical staining. For staining, after deparaffinization with citrosol (CitriSolv Hybrid™, Decon Labs), the tissue containing slides were incubated in Bouin's solution (Bouin's Fixative, Electron Microscopy Sciences) for 24 h at room temperature. Staining was done as follows: hematoxylin (Harris Hematoxylin Solution, Sigma-Aldrich), Bibrich Scarlet Acid Fuchsin (Electron Microscopy Sciences), followed by aniline blue (Electron Microscopy Sciences).

SUMMARY

Disclosed herein is a bioprinter as a technology platform that enables the controllable in-situ deposition of architected, layered biomaterials and layered tissues onto target surfaces. Available biopolymer deposition rates are 0.3-1.6 cm$^2$/s depending on the cartridge used and printer forward speed, which exceed the ones of most extrusion-based bioprinters by at least one order of magnitude. While demonstrated for fibroblasts and keratinocytes in the skin context, the present inventors contemplate this approach is compatible with a wide range of cell types. Beyond the employed biomaterials, the inventors contemplate a wide range of natural and synthetic biopolymer solutions to be compatible with the presently disclosure.

An engineered skin substitute (ESS) is readily deposited onto either flat surfaces (in-vitro) or wound beds (in-vivo). The approach side steps the otherwise required additional washing and incubation steps as well as intricate manipulation of the weak and large-aspect ratio constructs. The ESS is prepared within minutes at clinically relevant rates. The reverse dermatome is straightforward to use and does not require complex in-situ scanning and multi-axis printhead translation. We anticipate the required level of operator training to be comparable with the one required for a regular dermatome.

The handheld tissue printer disclosed herein is a compact instrument (weight less than 0.8 kg) designed for routine use in operating rooms. The in-vivo results obtained for the selected case study of biopolymer deposition onto a porcine wound model suggest the method to be conducive to the delivery of cells, growth factors, and extracellular matric materials (ECMs) for wound healing studies in a clinical setting.

This description is exemplary and should not be interpreted as limiting the invention or its applications. Specific parts or part numbers mentioned in the description may be substituted by functional equivalents.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1 Svensjö, T. et al. Autologous skin transplantation: comparison of minced skin to other techniques. *Journal of Surgical Research* 103, 19-29 (2002).
2 Yannas, I., Burke, J., Orgill, D. & Skrabut, E. Wound tissue can utilize a polymeric template to synthesize a functional extension of skin. *Science* 215, 174-176 (1982).
3 Gerlach, J. C. et al. Method for autologous single skin cell isolation for regenerative cell spray transplantation with non-cultured cells. *The International Journal of Artificial Organs* 34, 271-279 (2011).
4 Murphy, S. V. & Atala, A. 3D bioprinting of tissues and organs. *Nature Biotechnology* 32, 773-785 (2014).
5 Tasoglu, S. & Demirci, U. Bioprinting for stem cell research. *Trends in Biotechnology* 31, 10-19 (2013).
6 Pati, F., Gantelius, J. & Svahn, H. A. 3D Bioprinting of Tissue/Organ Models. *Angewandte Chemie-International Edition* 55, 4650-4665, doi:10.1002/anie.201505062 (2016).
7 Kang, H. W. et al. A 3D bioprinting system to produce human-scale tissue constructs with structural integrity. *Nature Biotechnology* 34, 312-+, doi:10.1038/nbt.3413 (2016).
8 Pataky, K. et al. Microdrop Printing of Hydrogel Bioinks into 3D Tissue-Like Geometries. *Advanced Materials* 24, 391-396 (2012).
9 Dhariwala, B., Hunt, E. & Boland, T. Rapid prototyping of tissue-engineering constructs, using photopolymerizable hydrogels and stereolithography. *Tissue Engineering* 10, 1316-1322 (2004).
10 Dendukuri, D., Pregibon, D. C., Collins, J., Hatton, T. A. & Doyle, P. S. Continuous-flow lithography for high-throughput microparticle synthesis. *Nature Materials* 5, 365-369 (2006).
11 Xu, T., Jin, J., Gregory, C., Hickman, J. J. & Boland, T. Inkjet printing of viable mammalian cells. *Biomaterials* 26, 93-99 (2005).
12 Boland, T., Xu, T., Damon, B. & Cui, X. Application of inkjet printing to tissue engineering. *Biotechnology Journal* 1, 910-917 (2006).

13 Odde, D. J. & Renn, M. J. Laser-guided direct writing for applications in biotechnology. *Trends in Biotechnology* 17, 385-389 (1999).

14 Barron, J. A., Ringeisen, B. R., Kim, H., Spargo, B. J. & Chrisey, D. B. Application of laser printing to mammalian cells. *Thin Solid Films* 453, 383-387 (2004).

15 Norotte, C., Marga, F. S., Niklason, L. E. & Forgacs, G. Scaffold-free vascular tissue engineering using bioprinting. *Biomaterials* 30, 5910-5917 (2009).

16 Melchels, F. P., Dhert, W. J., Hutmacher, D. W. & Malda, J. Development and characterisation of a new bioink for additive tissue manufacturing. *Journal of Materials Chemistry B* 2, 2282-2289 (2014).

17 Ferris, C. J., Gilmore, K. J., Beirne, S., McCallum, D. & Wallace, G. G. Bio-ink for on-demand printing of living cells. *Biomaterials Science* 1, 224-230 (2013).

18 Onoe, H. et al. Metre-long cell-laden microfibres exhibit tissue morphologies and functions. *Nature Materials* 12, 584-590 (2013).

19 Yu, L. & Ding, J. Injectable hydrogels as unique biomedical materials. *Chemical Society Reviews* 37, 1473-1481 (2008).

20 Griffin, D. R., Weaver, W. M., Scumpia, P. O., Di Carlo, D. & Segura, T. Accelerated wound healing by injectable microporous gel scaffolds assembled from annealed building blocks. *Nature Materials* 14, 737-744 (2015).

21 Navarro, F. et al. Sprayed keratinocyte suspensions accelerate epidermal coverage in a porcine microwound model. *Journal of Burn Care & Research* 21, 513 (2000).

22 Falanga, V. et al. Autologous bone marrow-derived cultured mesenchymal stem cells delivered in a fibrin spray accelerate healing in murine and human cutaneous wounds. *Tissue Engineering* 13, 1299-1312 (2007).

23 Lee, S.-H. & Shin, H. Matrices and scaffolds for delivery of bioactive molecules in bone and cartilage tissue engineering. *Advanced Drug Delivery Reviews* 59, 339-359 (2007).

24 de las Heras Alarcon, C., Farhan, T., Osborne, V. L., Huck, W. T. S. & Alexander, C. Bioadhesion at micropatterned stimuli-responsive polymer brushes. *Journal of Materials Chemistry* 15, 2089-2094 (2005).

25 Foster, K. et al. Efficacy and safety of a fibrin sealant for adherence of autologous skin grafts to burn wounds: results of a phase 3 clinical study. *Journal of Burn Care & Research* 29, 293-303 (2008).

26 Wijnen, B., Hunt, E. J., Anzalone, G. C. & Pearce, J. M. Open-source syringe pump library. *PloS One* 9, e107216 (2014).

27 Au, A. K., Huynh, W., Horowitz, L. F. & Folch, A. 3D-printed microfluidics. *Angewandte Chemie International Edition* (2016).

28 Batchelor, G. K. *An introduction to fluid dynamics.* (Cambridge University Press, 2000).

29 Knight, J. B., Vishwanath, A., Brody, J. P. & Austin, R. H. Hydrodynamic focusing on a silicon chip: mixing nanoliters in microseconds. *Physical Review Letters* 80, 3863 (1998).

30 Leng, L., McAllister, A., Zhang, B., Radisic, M. & Gunther, A. Mosaic hydrogels: one-step formation of multiscale soft materials. *Advanced Materials* 24, 3650-3658 (2012).

31 Slaughter, B. V., Khurshid, S. S., Fisher, O. Z., Khademhosseini, A. & Peppas, N A. Hydrogels in regenerative medicine. *Advanced Materials* 21, 3307-3329 (2009).

32 Tremblay, D., Cuerrier, C. M., Andrzejewski, L., O'Brien, E. R. & Pelling, A. E. A novel stretching platform for applications in cell and tissue mechanobiology. *Journal of Visualized Experiments*, e51454-e51454 (2014).

33 Emerson, D. R., Cieślicki, K., Gu, X. & Barber, R. W. Biomimetic design of microfluidic manifolds based on a generalised Murray's law. *Lab on a Chip* 6, 447-454 (2006).

34 Pinkus, O. The Reynolds Centennial—a Brief-History of the Theory of Hydrodynamic Lubrication. *J Tribol-T ASME* 109, 2-20 (1987).

Therefore what is claimed is:

1. A handheld bioprinter for controlled in-situ formation and deposition of biopolymeric sheets and planar tissues on surfaces, comprising:
    a) support frame and a printhead attached to said support frame, said printhead including a first array of extrusion channels and at least a second array of extrusion channels located with respect to said first array such that in operation said first array is proximally adjacent to said surface, an end section of said printhead having a width W such that said first and second arrays span said width W;
    b) a first reservoir of biopolymer attached to said frame, said first array of extrusion channels being in flow communication with said first reservoir of biopolymer to be extruded onto the surface, a second reservoir of liquid attached to said frame, said second array being in flow communication with said second reservoir of liquid to be extruded along with the extruded biopolymer, and including a first dispensing mechanism associated with said first reservoir being configured to dispense biopolymer at a flow rate of QM, and a second dispensing mechanism associated with said second reservoir being configured to dispense the liquid at a flow rate of QC;
    c) a drive mechanism attached to said frame such that when activated by the operator, said printhead is driven along the surface located a vertical height H above the surface at a preselected velocity V;
    d) a controller connected to said drive mechanism and said first dispensing mechanism and programmed such upon activating said drive mechanism, said first dispensing mechanism dispenses biopolymer at the flow rate QM a layer of thickness t, which satisfies the condition $QM = W \cdot V \cdot H \ (6(t/H) - 6(t/H)2 + 3(t/H)2(\mu c/\mu M))/(6(t/H) \ (\mu c/\mu M) - 6(t/H) + 6)$.

2. The bioprinter according to claim 1, wherein said drive mechanism is configured to provide variable velocities V, and wherein said controller is programmed with instructions to control said first dispensing mechanism to responsively adjust said flow rate QM such that for a given velocity V said flow rate conditions are maintained.

3. The bioprinter according to claim 1 wherein said second dispensing mechanism is operably coupled with said controller and is configured to dispense the liquid at said flow rate QC which satisfies the condition $$QC = 0.5 \ W \cdot V \cdot (H - t).$$

4. The bioprinter according to claim 3, wherein said drive mechanism is configured to provide variable velocities V, and wherein said controller is programmed with instructions to control said first and second dispensing mechanisms to responsively adjust said flow rates QM and QC such that for a given velocity V said conditions are maintained.

5. The bioprinter according to claim 1, wherein said end section of said printhead includes an overhanging section extending outwardly from a top surface of said second array, said overhanging section extending outwardly from said end section by a length L.

6. The bioprinter according to claim 5, wherein L is equal to or greater than the value of H.

7. The bioprinter according to claim 1, wherein said first array of extrusion channels are in flow communication with said first reservoir via a bifurcating channel network comprised of a first channel connected to said first reservoir which bifurcates into two channels which further bifurcates until a final number of channels equals a number of extrusion channels in said first array, and an end of each channel is adjacent an end of a corresponding extrusion channel in said first array, and wherein said second array of extrusion channels are in flow communication with said second reservoir via a bifurcating channel network comprised of a first channel connected to said second reservoir which bifurcates into two channels which further bifurcates until a final number of channels equals a number of extrusion channels in said second array, and an end of each channel is adjacent an end of a corresponding extrusion channel in said second array.

8. The bioprinter according to claim 7 wherein hydraulic diameters of the channels in the bifurcating channel networks decrease from each inlet to each exit going from said reservoir to said print head in accordance with Murray's law.

9. The bioprinter according to claim 7, further comprising a handle configured to allow a user to grasp and use the bioprinter during dispensing operations.

10. The bioprinter according claim 9 wherein said drive mechanism comprises a pair of axel mounted rollers connected to said drive mechanism, and wherein said printhead is positioned between said rollers, and wherein said end section includes a circular guidance feature maintains a consistent gap height between the channel device exit and deposition surface regardless of changing the deposition angle, and wherein during operation upon activation of said drive mechanism, said pair of axel mounted rollers are rotationally driven such that the handheld bioprinter moves along the surface at said velocity V.

11. The bioprinter according to claim 9, wherein said drive mechanism comprises a roller connected to said drive mechanism, and wherein said roller is positioned behind said printhead, and wherein end section contains a circular guidance feature to maintain a consistent gap height between the channel device exit and deposition surface regardless of changing the deposition angle, and wherein during operation upon activation of said drive mechanism, said roller is rotationally driven such that the handheld bioprinter moves along the surface at said velocity V.

12. The bioprinter according to claim 9, wherein said drive mechanism comprises a translation mechanism attached to said frame, said print head being mounted on said translation mechanism, said translation mechanism being configured to move said print head at said velocity V with respect to said surface.

13. The bioprinter according to claim 2, wherein said exit section of said printhead including an overhanging section extending outwardly from a top surface of said second array, said overhanging protruding section extending outwardly from said exit section by a length L.

14. The bioprinter according to claim 13, wherein L is equal to or greater than the value of H.

15. The bioprinter according to claim 3, wherein said end section of said printhead includes an overhanging section extending outwardly from a top surface of said second array, said overhanging section extending outwardly from said end section by a length L.

16. The bioprinter according to claim 4, wherein said end section of said printhead includes an overhanging section extending outwardly from a top surface of said second array, said overhanging section extending outwardly from said end section by a length L.

17. The bioprinter according to claim 2, wherein said first array of extrusion channels are in flow communication with said first reservoir via a bifurcating channel network comprised of a first channel connected to said first reservoir which bifurcates into two channels which further bifurcates until a final number of channels equals a number of extrusion channels in said first array, and an end of each channel is adjacent an end of a corresponding extrusion channel in said first array, and wherein said second array of extrusion channels are in flow communication with said second reservoir via a bifurcating channel network comprised of a first channel connected to said second reservoir which bifurcates into two channels which further bifurcates until a final number of channels equals a number of extrusion channels in said second array, and an end of each channel is adjacent an end of a corresponding extrusion channel in said second array.

18. The bioprinter according to claim 3, wherein said first array of extrusion channels are in flow communication with said first reservoir via a bifurcating channel network comprised of a first channel connected to said first reservoir which bifurcates into two channels which further bifurcates until a final number of channels equals a number of extrusion channels in said first array, and an end of each channel is adjacent an end of a corresponding extrusion channel in said first array, and wherein said second array of extrusion channels are in flow communication with said second reservoir via a bifurcating channel network comprised of a first channel connected to said second reservoir which bifurcates into two channels which further bifurcates until a final number of channels equals a number of extrusion channels in said second array, and an end of each channel is adjacent an end of a corresponding extrusion channel in said second array.

19. The bioprinter according to claim 4, wherein said first array of extrusion channels are in flow communication with said first reservoir via a bifurcating channel network comprised of a first channel connected to said first reservoir which bifurcates into two channels which further bifurcates until a final number of channels equals a number of extrusion channels in said first array, and an end of each channel is adjacent an end of a corresponding extrusion channel in said first array, and wherein said second array of extrusion channels are in flow communication with said second reservoir via a bifurcating channel network comprised of a first channel connected to said second reservoir which bifurcates into two channels which further bifurcates until a final number of channels equals a number of extrusion channels in said second array, and an end of each channel is adjacent an end of a corresponding extrusion channel in said second array.

20. The bioprinter according to claim 5, wherein said first array of extrusion channels are in flow communication with said first reservoir via a bifurcating channel network comprised of a first channel connected to said first reservoir which bifurcates into two channels which further bifurcates until a final number of channels equals a number of extrusion channels in said first array, and an end of each channel is adjacent an end of a corresponding extrusion channel in said first array, and wherein said second array of extrusion channels are in flow communication with said second reservoir via a bifurcating channel network comprised of a first channel connected to said second reservoir which bifurcates into two channels which further bifurcates until a final number of channels equals a number of extrusion channels in said second array, and an end of each channel is adjacent an end of a corresponding extrusion channel in said second array.

* * * * *